(12) United States Patent
Fei et al.

(10) Patent No.: US 11,604,189 B2
(45) Date of Patent: Mar. 14, 2023

(54) DETECTION DEVICE CAPABLE OF VISUAL TEST RESULTS

(71) Applicant: LEADWAY (HK) LIMITED, Hong Kong (CN)

(72) Inventors: Feng qin Fei, Hangzhou Zhejiang (CN); Chunxia Zhang, Hangzhou Zhejiang (CN); Tao Shang, Hangzhou Zhejiang (CN)

(73) Assignee: LEADWAY (HK) LIMITED, Hong Kong (CN)

( * ) Notice: Subject to any disclaimer, the term of this patent is extended or adjusted under 35 U.S.C. 154(b) by 525 days.

(21) Appl. No.: 16/608,148

(22) PCT Filed: Apr. 26, 2018

(86) PCT No.: PCT/CN2018/084598
§ 371 (c)(1),
(2) Date: Oct. 24, 2019

(87) PCT Pub. No.: WO2018/196802
PCT Pub. Date: Nov. 1, 2018

(65) Prior Publication Data
US 2020/0150048 A1    May 14, 2020

(30) Foreign Application Priority Data

Apr. 28, 2017   (CN) .................. 201710296044.7
Apr. 28, 2017   (CN) .................. 201710297068.4

(51) Int. Cl.
*G01N 33/543*   (2006.01)
*G01N 21/78*    (2006.01)
(Continued)

(52) U.S. Cl.
CPC ....... *G01N 33/54388* (2021.08); *G01N 21/78* (2013.01); *G01N 21/8483* (2013.01);
(Continued)

(58) Field of Classification Search
CPC .............. G01N 21/78; G01N 21/8483; G01N 2021/7756; G01N 33/54387;
(Continued)

(56) References Cited

U.S. PATENT DOCUMENTS 4,223,089 A   9/1980 Rothe et al.
4,426,451 A   1/1984 Columbus
(Continued)

FOREIGN PATENT DOCUMENTS

CN    1682114 A     10/2005
CN    2849725 Y     12/2006
(Continued)

OTHER PUBLICATIONS

International Search Report dated Jul. 20, 2018 in PCT/CN2018/084598 with English translation (10 pages).
(Continued)

*Primary Examiner* — Jennifer Wecker
*Assistant Examiner* — Michelle Adams
(74) *Attorney, Agent, or Firm* — Acuity Law Group, PC; Michael A. Whittaker

(57) ABSTRACT

A detection device (10), comprising a sample detection layer (1) provided thereon with a detection reagent reacted with an analyte and a result display region (18), wherein the device further comprises a symbol display layer (2) on which an indicator (21) is processed; after the indicator contacts with a gas which can change the color of the indicator, the indicator changes from a first color to a second color.

11 Claims, 11 Drawing Sheets

Figure 1:
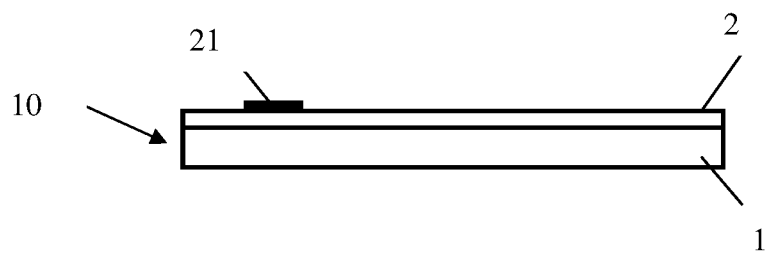

(51) Int. Cl.
  *G01N 21/84* (2006.01)
  *G01N 21/77* (2006.01)
  *G01N 33/76* (2006.01)

(52) U.S. Cl.
  CPC ..... *G01N 33/76* (2013.01); *G01N 2021/7756* (2013.01); *G01N 2021/7759* (2013.01); *G01N 2470/04* (2021.08)

(58) Field of Classification Search
  CPC ....... G01N 33/54388; G01N 33/54389; G01N 33/54391; G01N 21/783; G01N 2021/8488; G01N 33/76; G01N 2021/7759; G01N 2470/04; G01N 2470/06; G01N 31/002; G01N 33/0054; Y10T 436/175383
  See application file for complete search history.

(56) References Cited

U.S. PATENT DOCUMENTS

| | | | |
|---|---|---|---|
| 4,719,085 A | | 1/1988 | Jacobs |
| 5,141,853 A | | 8/1992 | Kasal et al. |
| 5,286,624 A | | 2/1994 | Terashima et al. |
| 5,660,790 A | | 8/1997 | Lawrence et al. |
| 5,989,840 A | * | 11/1999 | D'Angelo ................ C12Q 1/04 422/50 |
| 6,852,281 B2 | | 2/2005 | Inoue et al. |
| 6,855,561 B2 | | 2/2005 | Jerome et al. |
| 7,255,832 B2 | | 8/2007 | Lawrence et al. |
| 7,297,502 B2 | | 11/2007 | Gao et al. |
| 7,537,937 B2 | | 5/2009 | Jerome et al. |
| 7,553,675 B2 | | 6/2009 | Jerome et al. |
| 8,454,903 B2 | | 6/2013 | Brewster et al. |
| 2003/0157699 A1 | * | 8/2003 | Jerome ................ G01N 33/558 435/287.2 |
| 2006/0029924 A1 | * | 2/2006 | Brewster .......... G01N 33/54306 435/287.1 |
| 2014/0311350 A1 | | 10/2014 | Campbell et al. |

FOREIGN PATENT DOCUMENTS

| | | | |
|---|---|---|---|
| CN | 1914508 A | | 2/2007 |
| CN | 101101244 A | | 1/2008 |
| CN | 201072413 Y | | 6/2008 |
| CN | 201072416 Y | | 6/2008 |
| CN | 101341407 A | | 1/2009 |
| CN | 201540288 U | | 8/2010 |
| CN | 1828301 B | | 10/2010 |
| CN | 102175821 A | | 9/2011 |
| CN | 101598727 B | | 10/2012 |
| CN | 101400997 B | | 4/2013 |
| CN | 102782474 B | | 1/2016 |
| CN | 104062427 B | | 1/2016 |
| CN | 206960361 U | * | 2/2018 |
| CN | 108802018 A | | 11/2018 |
| CN | 108802027 A | | 11/2018 |
| EP | 3617694 A1 | | 3/2020 |
| WO | WO-9854563 A1 | * | 12/1998 ............... C12Q 1/04 |
| WO | 2003/023371 | | 3/2003 |
| WO | 2005029068 A2 | | 3/2005 |
| WO | 2005066625 A1 | | 7/2005 |
| WO | 2018196802 A1 | | 11/2018 |

OTHER PUBLICATIONS

Extended European Search Report issued in EP 18791660 dated Nov. 30, 2020.
1st Office Action issued by SIPO in PRC Patent Application No. 201710296044.7 dated Apr. 10, 2019—incl Engl lang transl.
International Search Report and Written Opinion issued in WO 2018196802 dated Aug. 1, 2018—incl Engl lang transl.
International Preliminary Report on Patentability issued in WO 2018196802 dated Oct. 29, 2019—incl Engl lang transl.
Response to 1st Office Action issued in PRC Patent Application No. 201710296044.7 dated Aug. 20, 2019—incl Engl lang transl.
2nd Office Action issued by SIPO in PRC Patent Application No. 201710296044.7 dated Jan. 16, 2020—incl Engl lang transl.
Response to 2nd Office Action issued in PRC Patent Application No. 201710296044.7 dated Mar. 31, 2020—incl Engl lang transl.
3rd Office Action issued by SIPO in PRC Patent Application No. 201710296044.7 dated Oct. 23, 2020—incl Engl lang transl.
Response to 3rd Office Action issued in PRC Patent Application No. 201710296044.7 dated Jan. 14, 2021—incl Engl lang transl.
1st Office Action issued by SIPO in PRC Patent Application No. 201710297068.4 dated May 14, 2020—incl Engl lang transl.
Response to 1st Office Action issued in PRC Patent Application No. 201710297068.4 dated Sep. 29, 2020—incl Engl lang transl.
2nd Office Action issued by SIPO in PRC Patent Application No. 201710297068.4 dated Jan. 15, 2021—incl Engl lang transl.

* cited by examiner

DETECTION DEVICE CAPABLE OF VISUAL TEST RESULTS

CROSS-REFERENCE TO RELATED MATTERS

The present invention is filed under 35 U.S.C. § 371 as the U.S. national phase of International Patent Application No. PCT/CN2018/084598, filed Apr. 26, 2018, which designated the United States and claims priority to Chinese Patent Application No. 201710297068.4, filed Apr. 28, 2017, and to Chinese Patent Application No. 201710296044.7, filed Apr. 28, 2017, each of which is hereby incorporated in its entirety including all tables, figures and claims.

FIELD OF THE INVENTION

The present invention relates to the field of detection, and in particular to a detection device for determining whether an analyte is present in a sample and a method of manufacturing a detection device, and a sample detection method for detecting a sample using the detection device.

BACKGROUND OF THE INVENTION

The existing detection device using the lateral flow method generally includes a test strip, a sample pad, a labelled pad, a detecting pad and a sample absorption pad are sequentially mounted on the test strip, and the detecting pad includes a detection line and a control line. The detection line is used to determine whether the analyte is present in the sample. If it is positive, it means that the analyte is present in the sample, and if it is negative, it means that the analyte is not present in the sample. The control line is used to check and confirm the success of this detection. In order to more visually show whether an analyte is present in the sample, there are several products changing a positive result of the detection line position from the "−" form to the "+" form. When the analyte is present, the detection result is displayed as "+", and when the analyte is not present in the sample, the detection result is displayed as "−". The displayed way of "+" and "−" is more consistent with the positive and negative result indicators that people are accustomed to.

In the patent of U.S. Pat. No. 7,537,937, another test piece is disposed under the detecting pad marked with the detection line, and the test piece has another color indication line perpendicular to the detection line. During detection, the principle of the detecting pad material to become transparent after liquid chromatography is used to show the indication line below it. When the analyte is not present in the sample, the detection line on the detecting pad does not appear, and the color indication line on the test piece under the detecting pad is displayed by the transparent detecting pad, and the whole detection result is represented by a "−" symbol. When the analyte is present in the sample, a detection line appears on the detecting pad, and the color indication line on the test piece under the detecting pad is also displayed by the transparent detecting pad simultaneously, and the detection line and the color indication line are cross displayed, and presented as "+" symbol. However, because the material of the test area also has a certain transparency in the dried situation, the indication line can be seen faintly just before the product detection, which will affect the appearance of the products.

In the patent of CN200510049177.1, the positive control area comprises a water-absorbing strip made of a water-absorbing material, the water-absorbing strip comprises a substance of one or more ingredients which display a first color when dry and a second color when wet, wherein the vertical indication line of the "+" product is treated on a layer of water-absorbing strips (water-absorbing paper) by using ink which changes color when encountering water, and then the water-absorbing paper is cut into the required line size and pasted under the detection area. During detection, on one hand, the water-absorbing paper is discolored, and on the other hand, the material in the detection area becomes transparent after liquid chromatography, so that the detection results are displayed in two ways: "+" and "−" respectively. The main problem of this processing manner is that the production process is complex, It needs a lot of steps to assemble and process to make it.

SUMMARY OF THE INVENTION

Based on the above problems, the present invention provides a new detection device and a method of manufacturing the detection device, to better implement detection and display of the detection device.

In one embodiment, the present invention provides a detection device comprising a sample detection layer, wherein a sample detection layer is provided with a detecting reagent which is reacted with an analyte and a result display area, and the device further comprises a symbol display layer, and the symbol display layer is treated with an indicator; after the indicator contacts with a gas which can change the color of the indicator, the indicator changes from a first color to a second color.

Preferably, when the sample is added to the sample detection layer for detection, a gas that causes the indicator change color is generated and contacts with the indicator to change the indicator from the first color to the second color.

Preferably, the detection device further includes a gas generating reagent, the said gas generating reagent generates a gas that causes the indicator change color.

Preferably, the indicator does not contact with the result display area of the sample detection layer.

Preferably, a gas channel is provided between the sample detection layer and the symbol display layer.

Preferably, a gas channel is provided between the result display area on the sample detection layer and the indicator area on the symbol display layer.

Preferably, the result display area on the sample detection layer corresponds to the position of the indicator area on the symbol display layer. In one embodiment, the position of the indicator and the position of the result display area are spatially superimposed or overlapped, that is, viewed vertically from above the symbol display layer, the result display area overlaps with the projection of indicator area, and more specifically, the indicator of the indicator area overlaps with the detection line of the result display area.

Preferably, the symbol display layer is located on the sample detection layer, and the symbol display layer is a transparent or translucent material that can observe the detection result of the sample detection layer, and when the indicator on the symbol display layer encounters the gas and becomes the second color, forms an identifiable symbol with the detection line on the sample detection layer.

Preferably, the identifiable symbol is a "+" or "−" symbol.

In some embodiments, the material of the symbol display layer is selected from a water-impermeable material or a water-permeable material. Preferably, the symbol display layer material is selected from a water-impermeable material.

In some embodiments, the symbol display layer material is selected from materials that are not gas-permeable or has a poor gas-permeable effect. When the symbol display layer is a material that is not gas-permeable or has a poor gas-permeable effect, the indicator may be added to the side of the symbol display layer that is in contact with the gas, that is, adjacent to the side of the sample detection layer (detecting pad). In other embodiments, the symbol display layer material is selected from gas-permeable materials. When the symbol display layer is a gas-permeable material, the indicator may be added to the side of the symbol display layer that is in contact with the gas or the other side thereof, or may be added in the middle of the symbol display layer or the middle that the two layers of the gas-permeable symbol display layer are superimposed. The color of the indicator changes after the gas passes through the gas-permeable material to contact with the indicator.

In some preferred embodiments, the symbol display layer material is selected from transparent, gas-impermeable materials, for example, PV, PP, film, etc., in which the indicator is treated on one side of the sample detection layer, the said side faces to the symbol display layer. In other preferred embodiments, the symbol display layer material is selected from a transparent, gas-permeable, water-impermeable material. For example, a water-permeable gas-impermeable film, a PTFE film, etc., the indicator is treated on either side of both sides of the symbol display layer.

In a preferred embodiment, a liquid barrier layer is disposed between the sample detection layer and the symbol display layer, and the liquid barrier layer material is selected from a transparent gas-permeable, water-impermeable material. With the liquid barrier layer, the indicator is separated from the detection layer, which is more advantageous for the indicator to be fixed on the symbol display layer. The liquid barrier layer may or may not contact with the symbol display layer and the sample detection layer. For example, the liquid barrier layer only contacts with the symbol display layer, or the liquid barrier layer only contacts with the sample detection layer, or the liquid barrier layer contacts with or does not contact with the symbol display layer and the liquid barrier layer.

Preferably, the pairwise combination of the indicator and the gas generating reagent is selected from an acid-base indicator and an acid-base reaction generating reagent. Preferably, the acid-base indicator is selected from bromothymol blue, bromocresol green, phenolphthalein, and the acid-base reaction generating reagent is selected from an alkaline buffer salt, or a combination of an ammonium salt and an alkaline buffer salt.

Preferably, the acid-base reaction generating reagent is treated on the sample detection layer; the said ammonium salt and the said alkaline buffer salt are separately treated on the sample detection layer, and the ammonium salt and the alkaline buffer salt do not contact before the sample is added to the sample detection layer.

Preferably, the sample detection layer comprises a detecting pad, and the result display area is located on the detecting pad.

Preferably, the sample detection layer further comprises a sample pad and a labelled pad; the sample pad and the labelled pad are sequentially connected upstream of the detecting pad.

Preferably, the sample detection layer further comprises a gas generating pad; the gas generating pad and the detecting pad are located upstream of the detecting pad Preferably, the gas generating pad is connected between the labelled pad and the detecting pad. Preferably, the symbol display layer covers on the detecting pad and the gas generating pad; a gas channel is provided between the symbol display layer and the detecting pad.

Preferably, the alkaline buffer salt and/or the ammonium salt are separately treated on one or two of the sample pad, the labelled pad, the gas generating pad or the detecting pad; when the ammonium salt and the alkaline buffer salt are treated on the same pad, a certain distance is provided between the both.

In a specific embodiment, when the acid-base reaction generating reagent is selected from an alkaline buffer salt, the alkaline buffer salt is treated on a sample pad, a labelled pad, a gas generating pad or a detecting pad.

In another specific embodiment, when the acid-base reaction generating reagent is selected from an ammonium salt and an alkaline buffer salt, the ammonium salt and the alkaline buffer salt are separately treated on one or two of a sample pad, a labelled pad, a gas generating pad, and a detecting pad; when the ammonium salt and the alkaline buffer salt are treated on the same pad, a certain distance is provided between the both, that is, the two are located at different positions.

In a preferred embodiment, the gas generating pad is treated with an ammonium salt. More preferably, the sample pad is treated with an alkaline buffer salt.

Preferably, the gas generating pad is treated with an alkaline buffer salt and an ammonium salt, and the said alkaline buffer salt and the ammonium salt are treated at different positions on the gas generating pad with a certain distance therebetween. Preferably, the sample detection layer further comprises a water absorbing pad, the water absorbing pad is connected downstream of the detecting pad; one end of the symbol display layer covers on the sample pad, and the other end covers on the water absorbing pad; the symbol display layer does not contact with the labelled pad, the detecting pad and the gas generating pad, forming a gas channel. In some preferred embodiments, the detection device further includes a gas generating pad; the gas generating pad is connected with the detecting pad in vertical flow relationship and the gas generating pad and the symbol display layer are disposed on both sides of the detecting pad.

Preferably, the sample pad is further included, and the sample pad is connected with a side of the gas generating pad, the said side is not connected with the detecting pad. Preferably, both ends of one side of the detecting pad have an adhesive block with viscidity; the symbol display layer is connected with the detecting pad by the adhesive block; and a gas channel is formed between the symbol display layer and the detecting pad.

In some modes of sample detection in vertical flow, when the sample is added to the detection layer, the sample preferably does not contact the symbol display layer, so it is necessary to open the symbol display layer and add the sample to the detection layer. Thus, a movable connection or perhaps a detachable connection of the sample detection layer to the symbol display layer that can make the symbol display layer to be detachable from the sample detection layer. The movable connection can have many structures, such as bonding, or snapping, or plugging which can be peeled off, etc. The sample detection layer and the symbol display layer can be connected movably at one end, and the other end is connected fixedly; or both ends may be movable connections.

In some embodiments, the alkaline buffer salt and/or the ammonium salt are separately treated on one or two of the sample pad, the gas generating pad or the detecting pad;

when the ammonium salt and the alkaline buffer salt are treated on the same pad, a certain distance is provided between the two pads.

Preferably, the ammonium salt is treated on a gas generating pad. Preferably, the gas generating pad is also treated with an alkaline buffer salt which is treated at different positions on the gas generating pad with the ammonium salt.

Preferably, the ammonium salt is treated on a sample pad. Preferably, the sample pad is also treated with an alkaline buffer salt which is treated at different positions on the sample pad with the ammonium salt.

Preferably, the ammonium salt is treated on a gas generating pad and the alkaline buffer salt is treated on the sample pad.

Preferably, the gas generating pad material is selected from one of nitrocellulose, polyester film, glass fiber or filter paper.

In the present invention, also provided a detection cassette comprising a bottom plate and a cover plate, and the detection device is located between the bottom plate and the cover plate, the detection device comprises a sample detection layer, and the sample detection layer is provided with a result display area, wherein, a symbol display layer is also included, the symbol display layer is treated with an indicator, the indicator does not contact with the result display area of the sample detection layer, and after the indicator contacts with the gas which can change the color of the indicator, the indicator changes from the first color to the second color.

Preferably, the symbol display layer is located on the cover plate, and the sample detection layer is located on the bottom plate.

Preferably, the sample detection layer comprises a detecting pad, and the result display area is located on the detecting pad.

Preferably, the sample detection layer further comprises a sample pad, a labelled pad and a water absorbing pad; the sample pad and the labelled pad are sequentially connected upstream of the detecting pad, and the water absorbing pad is connected downstream of the detecting pad.

Preferably, the sample pad is treated with one or two of an ammonium salt and an alkaline buffer salt; the ammonium salt and alkaline buffer salt are treated at different positions on the sample pad.

Preferably, the sample detection layer further comprises a gas generating pad; the gas generating pad is located between the labelled pad and the detecting pad.

Preferably, the ammonium salt is treated on a gas generating pad and the alkaline buffer salt is treated on the sample pad.

Preferably, the cover plate of the detection cassette has a window and a sample adding hole, and the window position corresponds to the detection result area, and the sample adding hole is located at the sample pad.

In addition, the present invention also provides a sample detecting method capable of visually reading a detection result, wherein, it comprises a detection device, the said detection device comprises a sample detection layer and a symbol display layer; the said symbol display layer is located on the said sample detection layer; an indicator is treated on the symbol display layer;

The fluid sample is applied and flows through the sample detection layer, and the sample detection is performed for the sample detection layer to generate a detection line;

At the same time, the detection device generates a gas that changes the color of the indicator;

The gas contacting with the indicator of the symbol display layer makes the indicator change from the first color to the second color;

The indicator of the second color is superimposed with the detection line to form an identifiable symbol.

Preferably, a gas generating reagent is also included, which reacts to generate a gas that causes the indicator change color when the sample is applied to the detection device.

Preferably, the gas generating reagent is treated in whole or in part on the sample detection layer.

Preferably, the indicator is selected from bromothymol blue, bromocresol green, phenolphthalein; and the gas generating reagent is selected from an alkaline buffer salt, a combination of an ammonium salt and an alkaline buffer salt.

Preferably, after the sample adding to the sample detection layer, an alkaline buffer salt is subsequently applied to the sample detection layer such that the alkaline buffer salt immediately follows with the fluid sample to flow through the sample detection layer.

Preferably, the sample detection layer comprises a sample pad, a labelled pad, a gas generating pad and a detecting pad sequentially connected; the ammonium salt is treated on the gas generating pad; the sample flows sequentially through the sample pad, the labelled pad, the gas generating pad and the detecting pad. A gas is generated on the gas generating pad, and the sample generates a detecting line on the detecting pad.

In another aspect, the present invention also provides a method of manufacturing a detection device, comprising:

(1) Preparing a sample detection layer: providing a detecting pad having a result display area, and adding a detection reagent reacted with the analyte to the detecting pad;

(2) Preparing a symbol display layer: providing a transparent or translucent carrier, preparing an indicator solution, and treating the indicator solution on the said carrier, the indicator changes from the first color to the second color after contacting with a gas which can change the color of the indicator;

(3) The sample detection layer in step 1 and the symbol display layer in step 2 are assembled together, and make the indicator and the result display area of the sample detection layer not contact;

(4) Providing a gas generating reagent capable of generating a gas which changes the color of the indicator.

Preferably, some or all of the gas generating reagent is treated on the detection layer. Preferably, the sample detection layer comprises a detecting pad, a sample pad and a labelled pad, the sample pad, the labelled pad and the detecting pad are sequentially connected with each other in a direction the liquid flows, and the gas generating reagent is treated at least on one of the sample pad, the labelled pad and the detecting pads.

Preferably, a gas generating pad is further included, the gas generating pad is installed at any previous position of the detecting pad, and the gas generating reagent is added to the gas generating pad.

Preferably, the position and size of the indicator on the symbol display layer is set according to the position of the detection line of the result display area on the detection layer; the indicator is formulated into a solution with a certain concentration, and uniformly coated on the symbol display layer according to the set position and size of indicator.

Preferably, the indicator is selected from bromothymol blue, bromocresol green, phenolphthalein, and the gas generating reagent is selected from an alkaline buffer salt, a combination of an ammonium salt and an alkaline buffer salt.

Preferably, the ammonium salt is selected from NH4Cl or ammonium carbonate, and the alkaline buffer is selected from Tris buffer.

Preferably, ammonium chloride or ammonium carbonate or the like is formulated into a 1% solution and treated on the sample detection layer.

Preferably, the material of the gas generating pad is selected from one of glass fiber, filter paper or polyester film.

Preferably, the symbol display layer material is selected from a transparent or translucent water-impermeable material.

Preferably, a liquid barrier layer is disposed between the sample detection layer and the symbol display layer, and the liquid barrier layer material is selected from a transparent gas-permeable, water-impermeable material.

The present invention also provides a method for visually reading a detection result, comprising a detection device, the said detection device comprising a sample detection layer and a symbol display layer; the said symbol display layer is located on the sample detection layer; an indicator is treated on the symbol display layer; after the indicator contacts with a gas which can change the color of the indicator, the said indicator changes from a first color to a second color, forming an identifiable sign with the detection result on the sample detection layer.

Preferably, a gas generating reagent is also included, which reacts when the sample is applied to the detection device to generate a gas that causes a color change of the indicator.

Preferably, the gas generating reagent is treated in all or part of the sample detection layer.

Preferably, the indicator is selected from bromothymol blue, bromocresol green, phenolphthalein; and the gas generating reagent is selected from an alkaline buffer salt, a combination of an ammonium salt and an alkaline buffer salt.

Preferably, the sample detection layer comprises a sample pad, a labelled pad, a gas generating pad and a detecting pad sequentially connected; the ammonium salt is treated on the gas generating pad; the sample flows sequentially through the sample pad, the labelled pad, the gas generating pad and the detecting pad. A gas is generated on the gas generating pad, and a detecting line is generated on the detecting pad by samples.

Beneficial Effect

The device and the detection cassette of the invention can make the detection result stable and display clearly, so that the ordinary operator can obtain the detection result more visually. Thereby, the detection device is used in a wider range of people and scope.

BRIEF DESCRIPTIONS OF THE DRAWINGS

Figure 2:
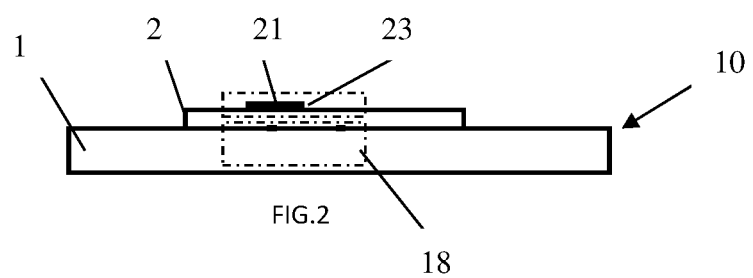
Figure 3:
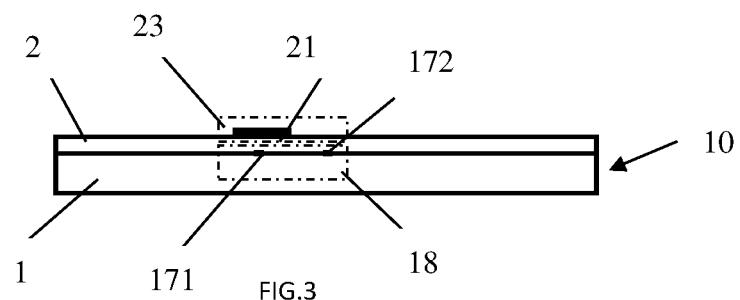
Figure 4:
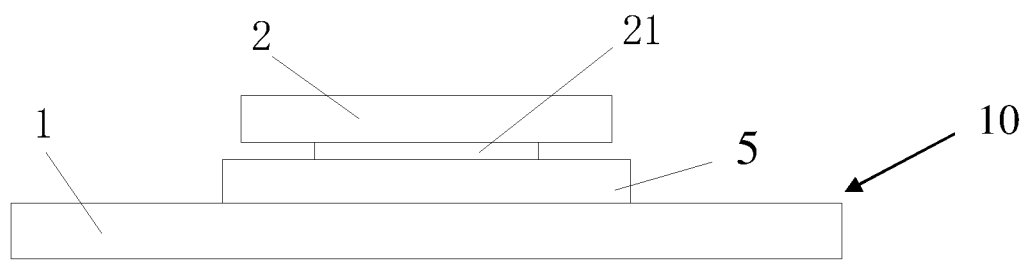
Figure 5:
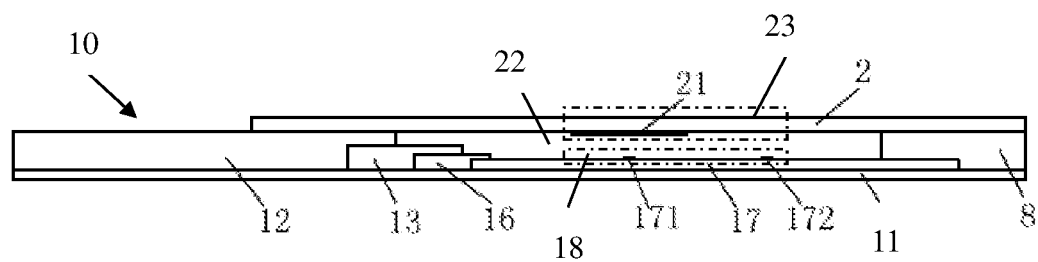
Figure 6:
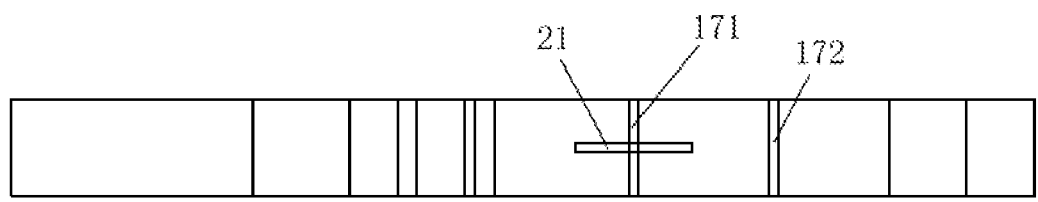
Figure 7:
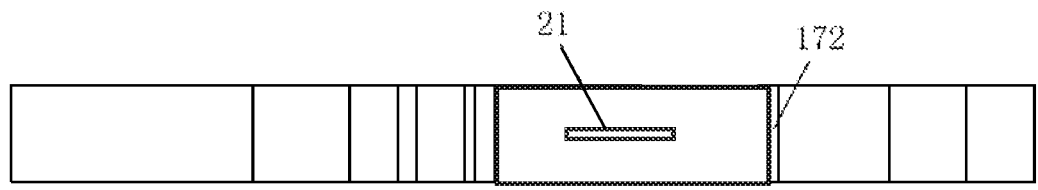
Figure 8:
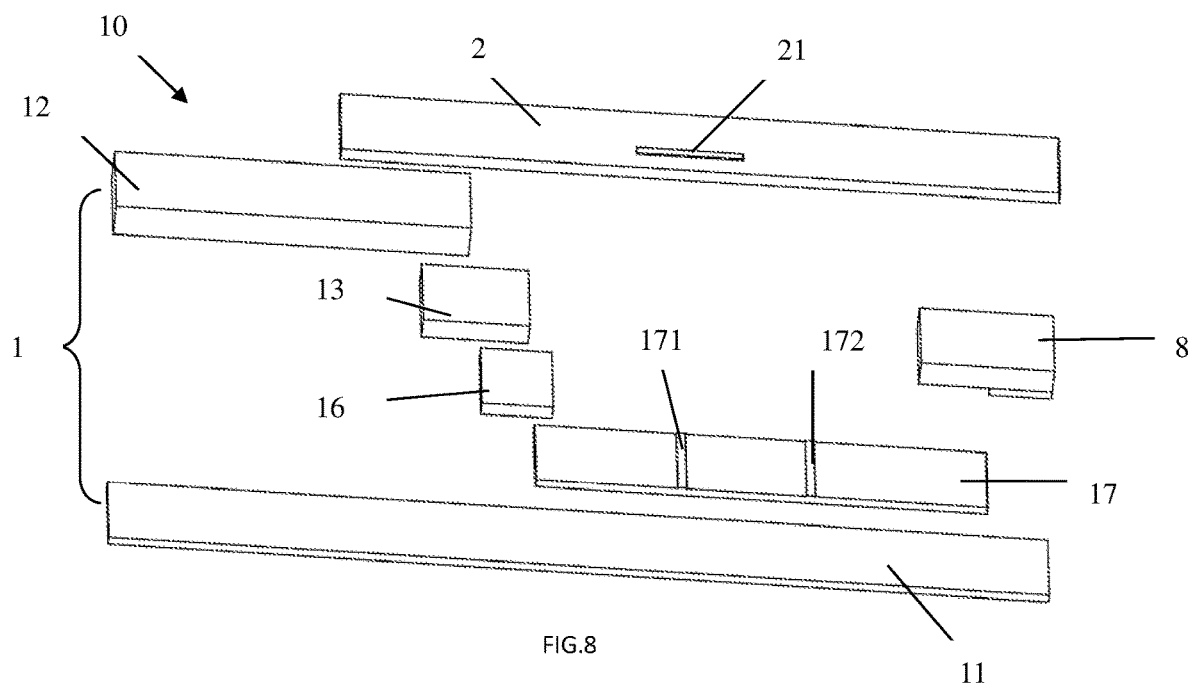
Figure 9:
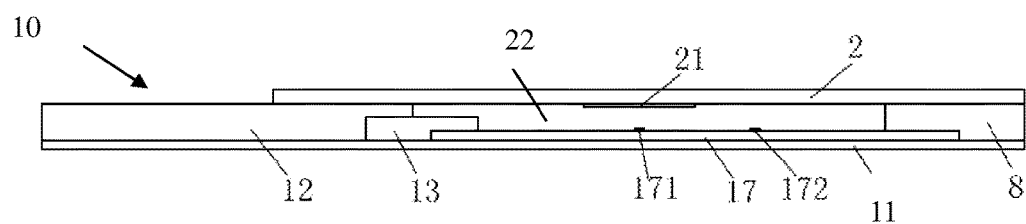
Figure 10:
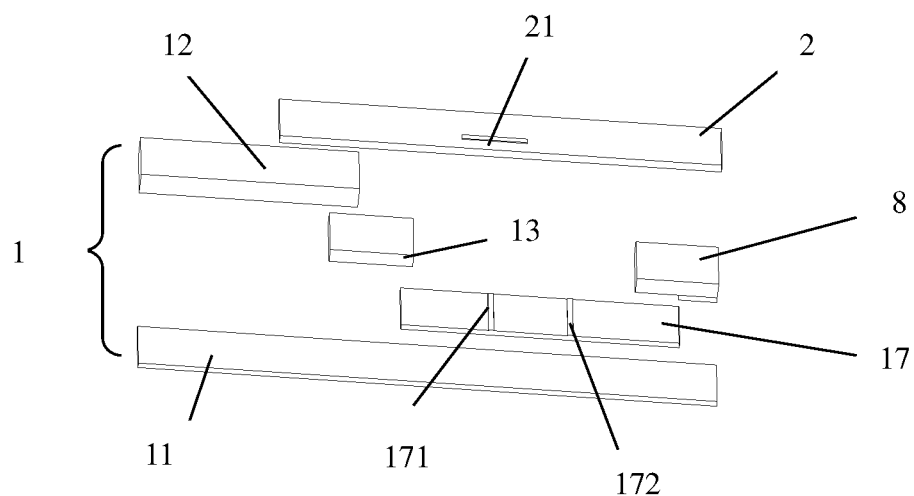
Figure 11:
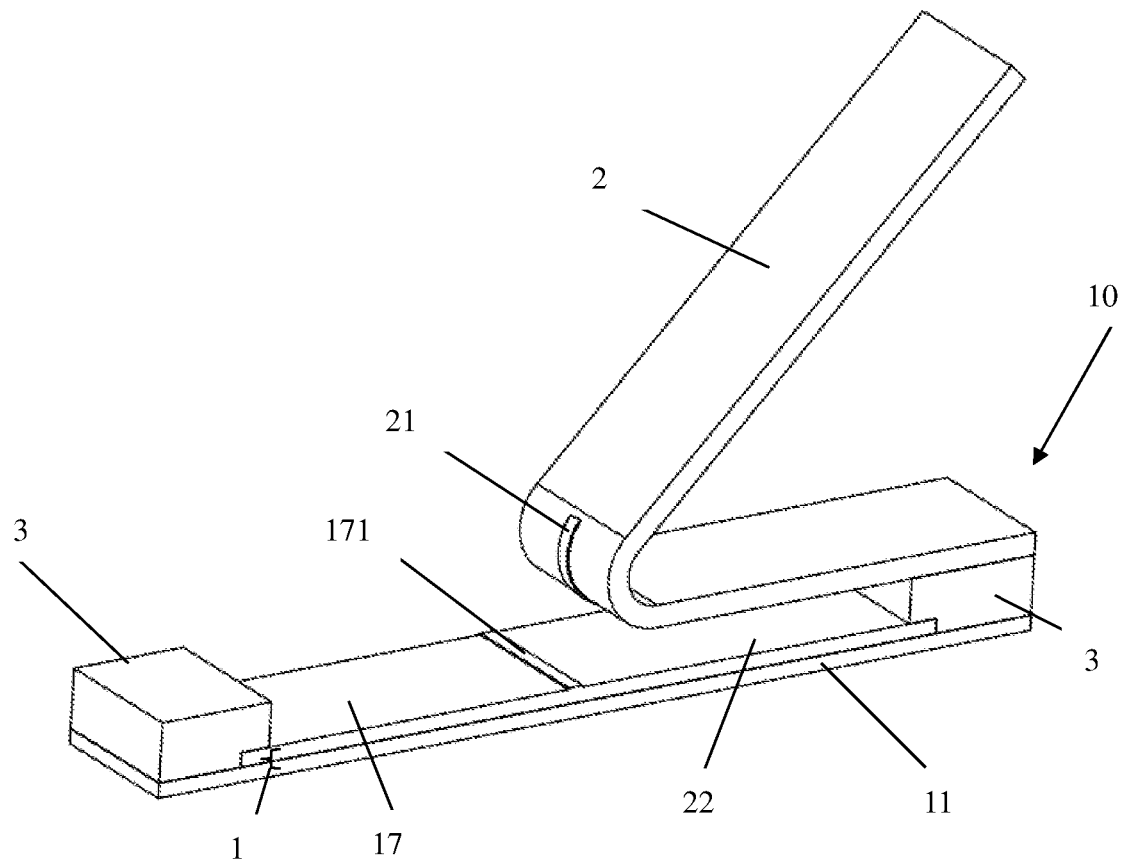
Figure 12:
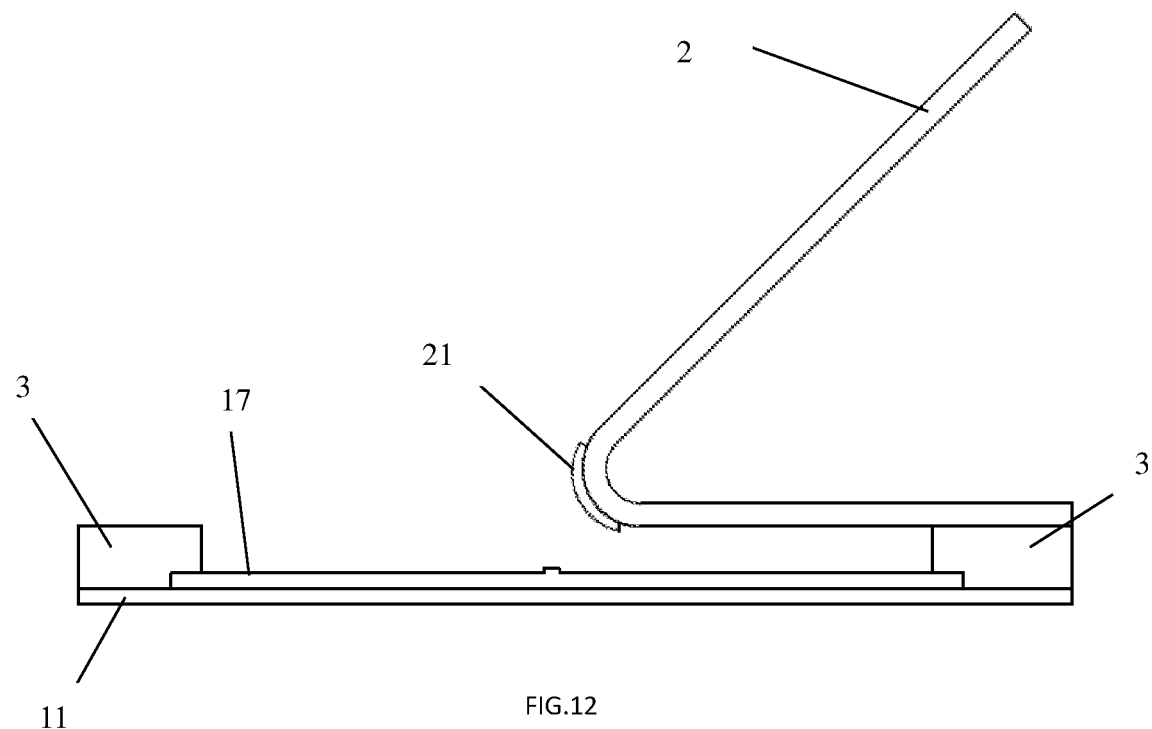
Figure 13:
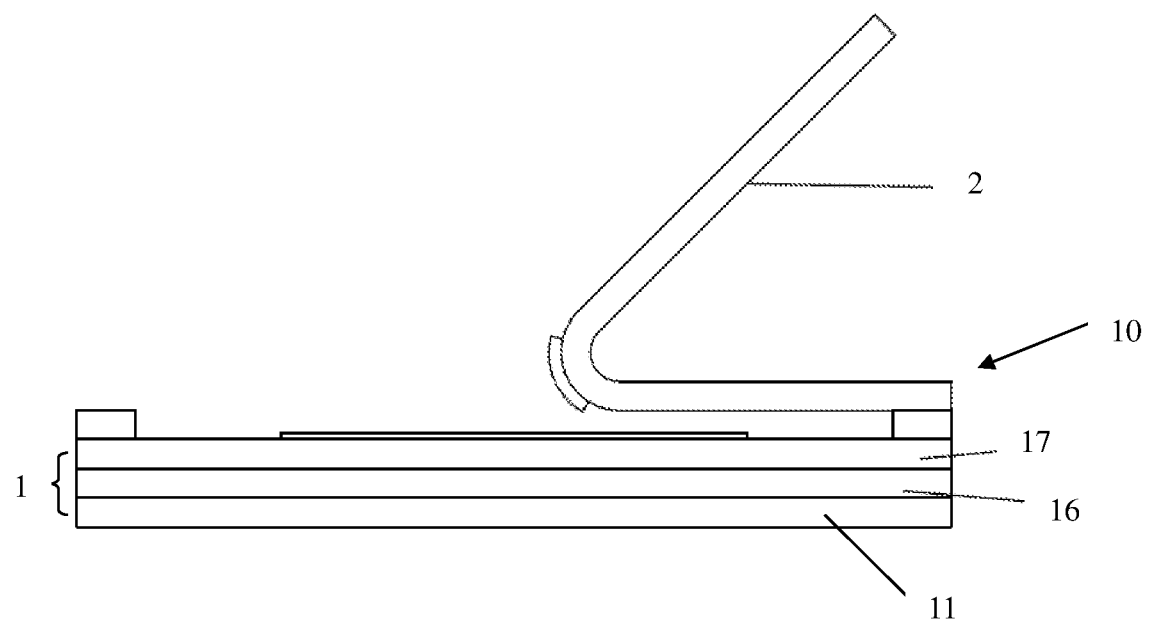
Figure 14:
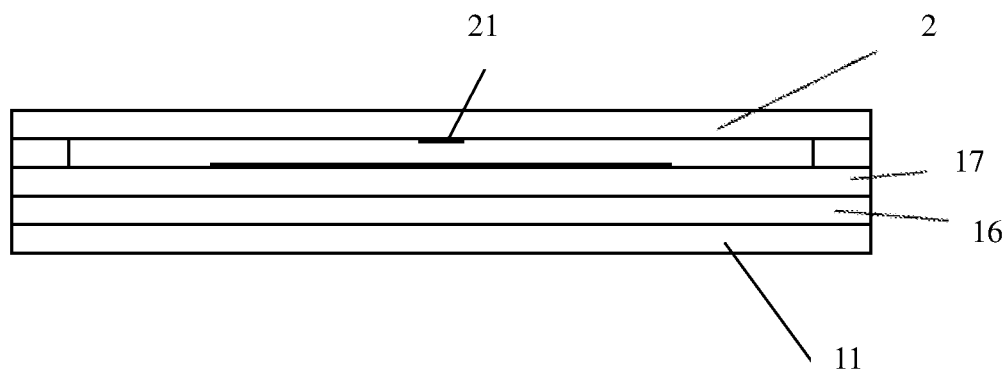
Figure 15:
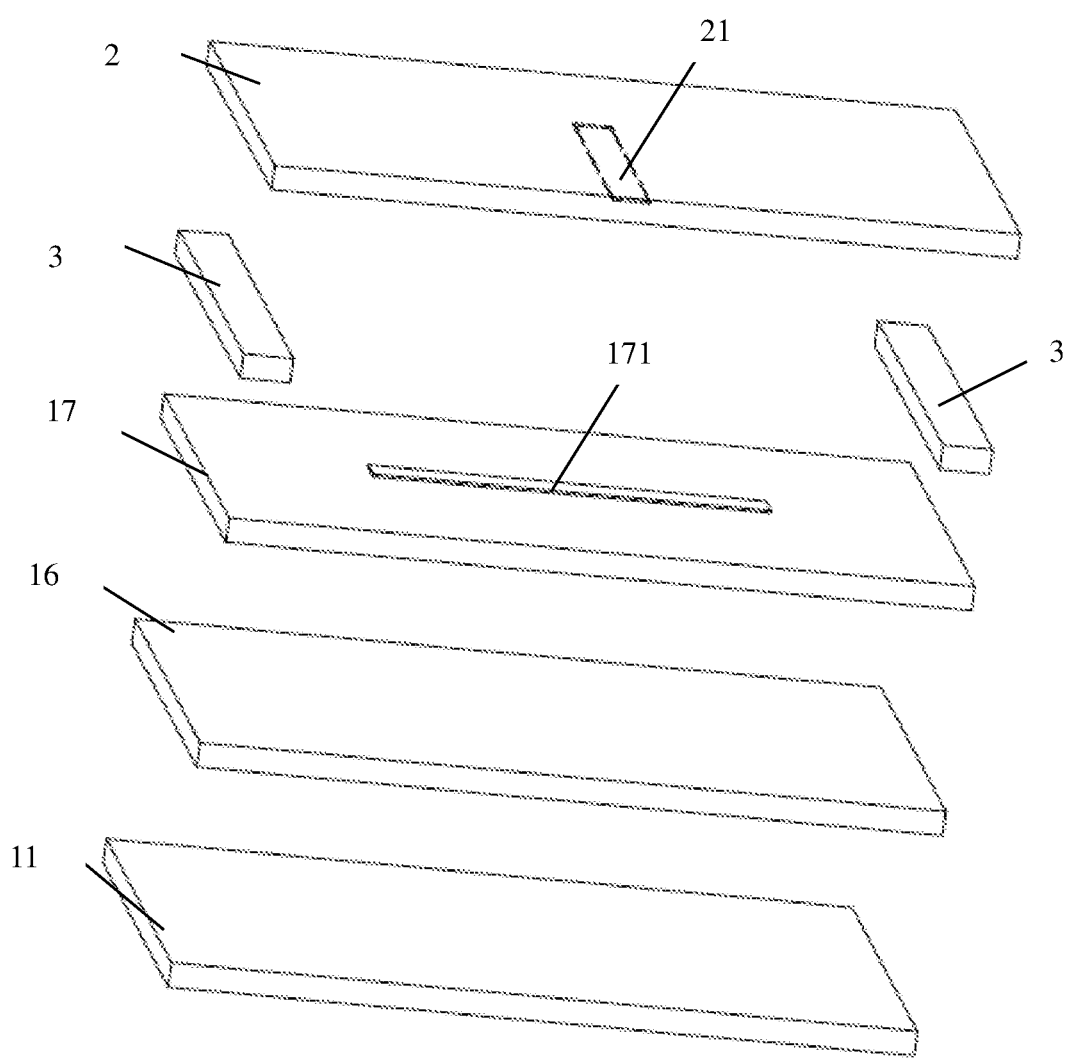
Figure 16:
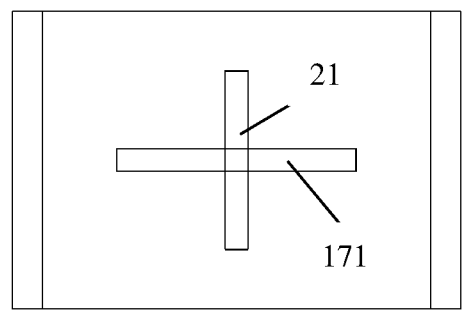
Figure 17:
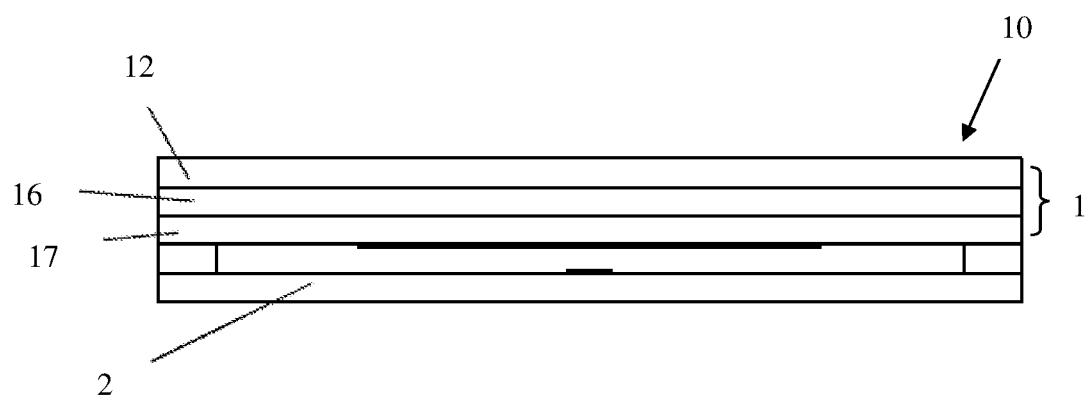
Figure 18:
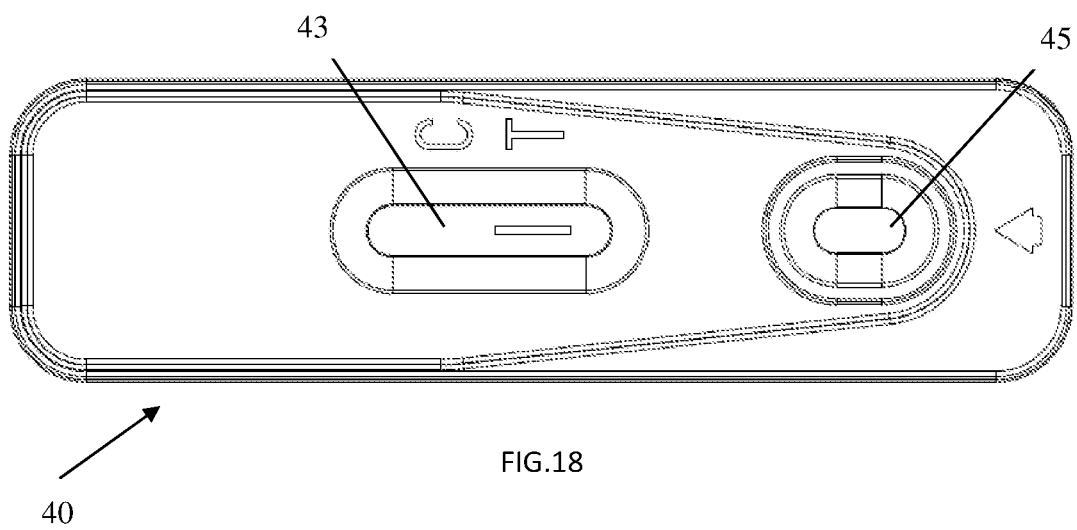
Figure 19:
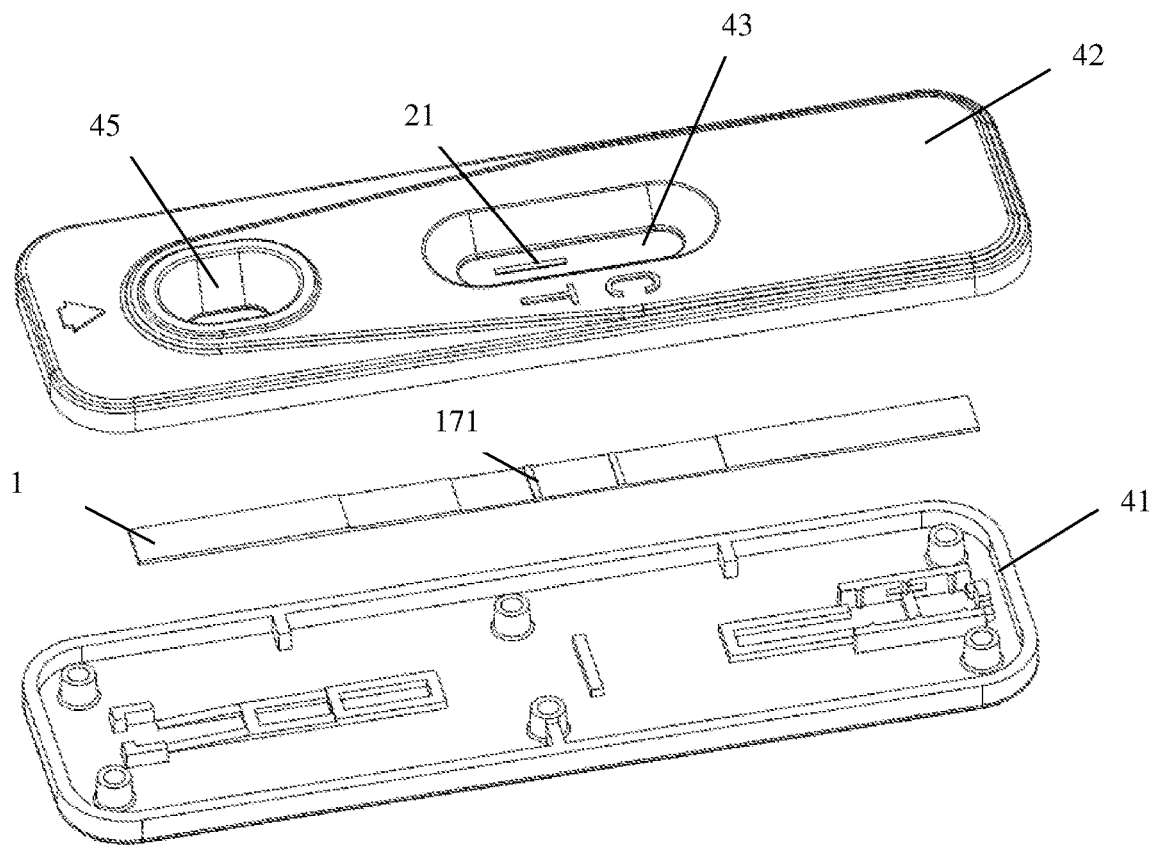
Figure 20:
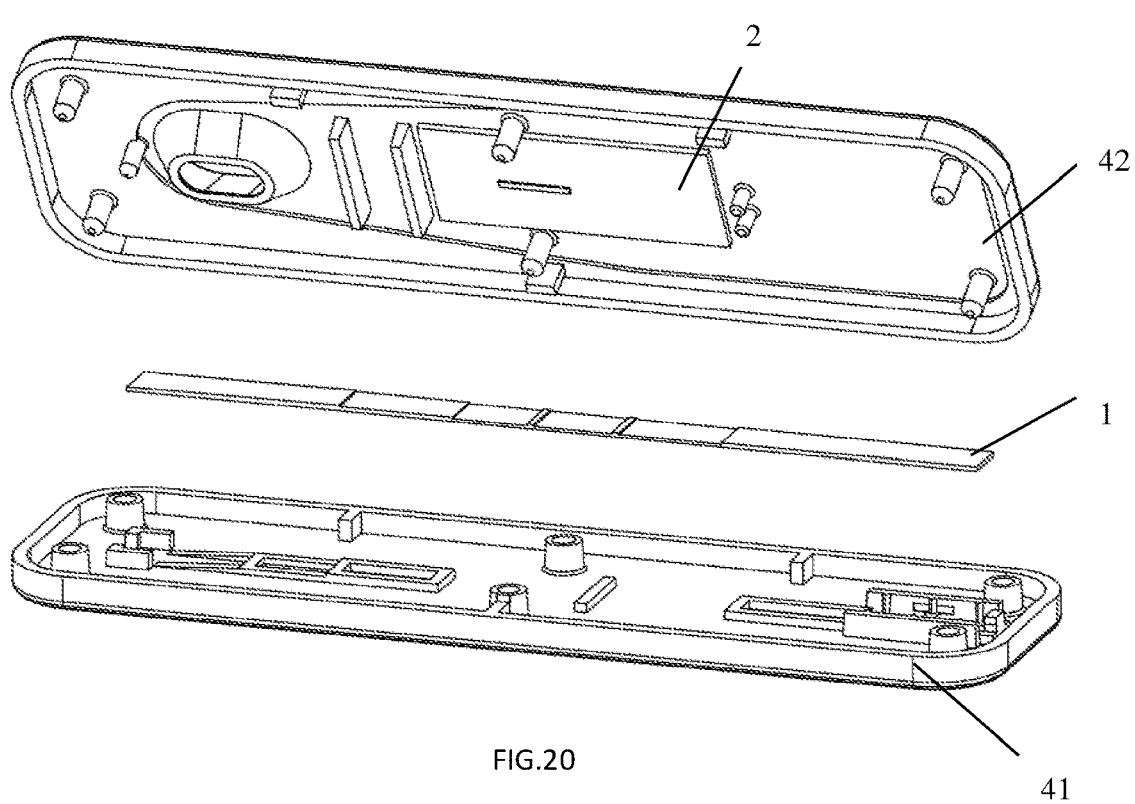
Figure 21:
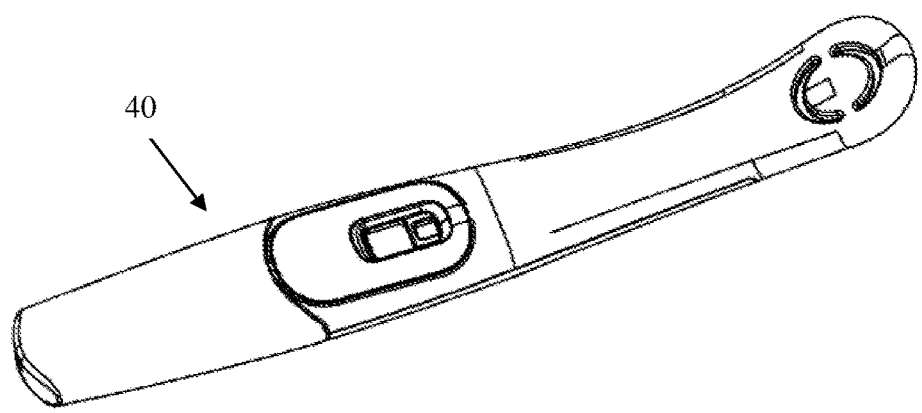
Figure 22:
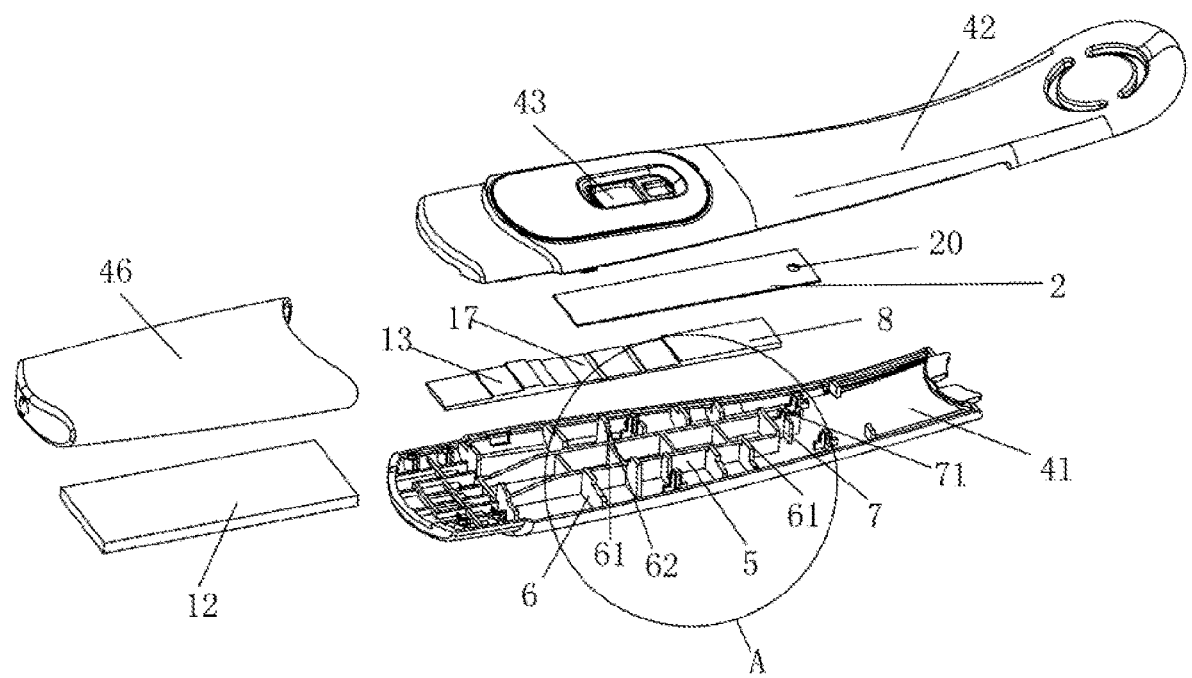
Figure 23:
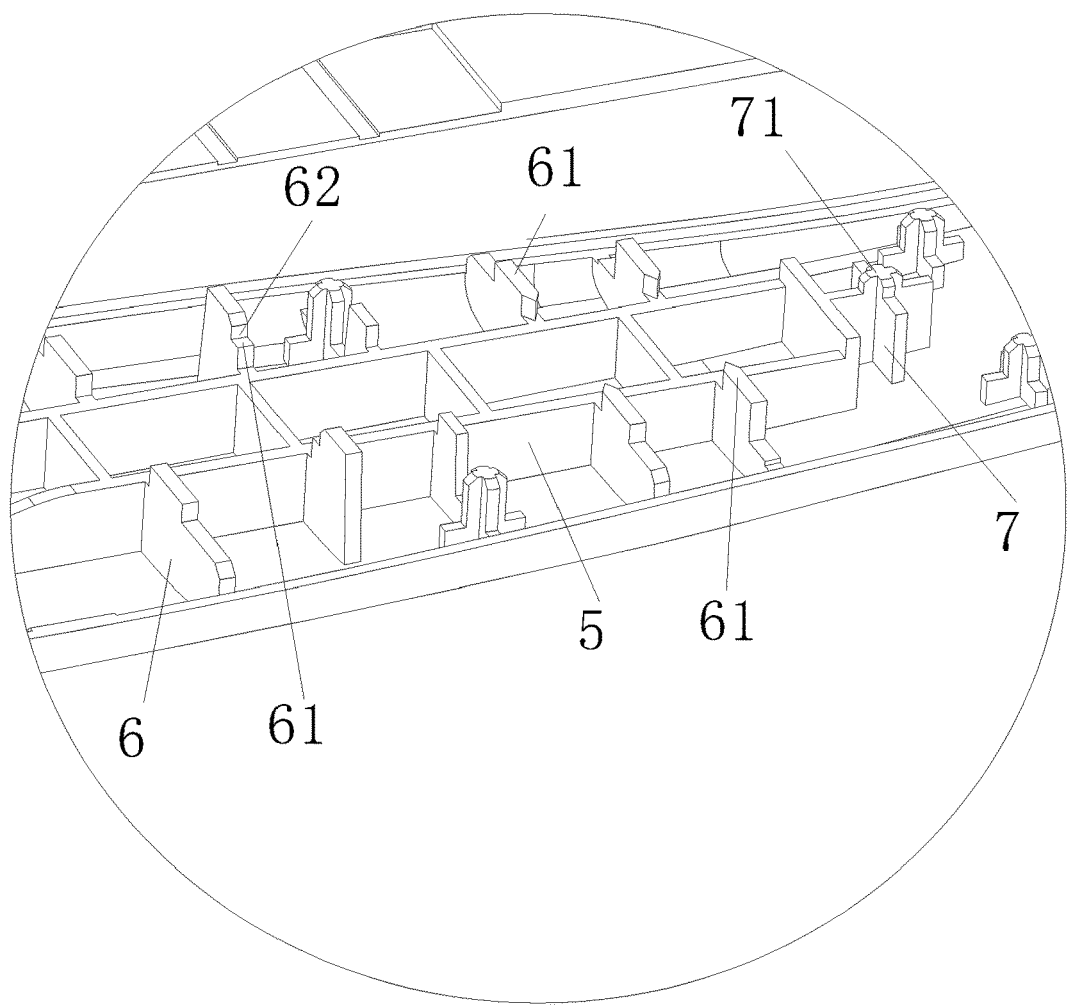
Figure 24:
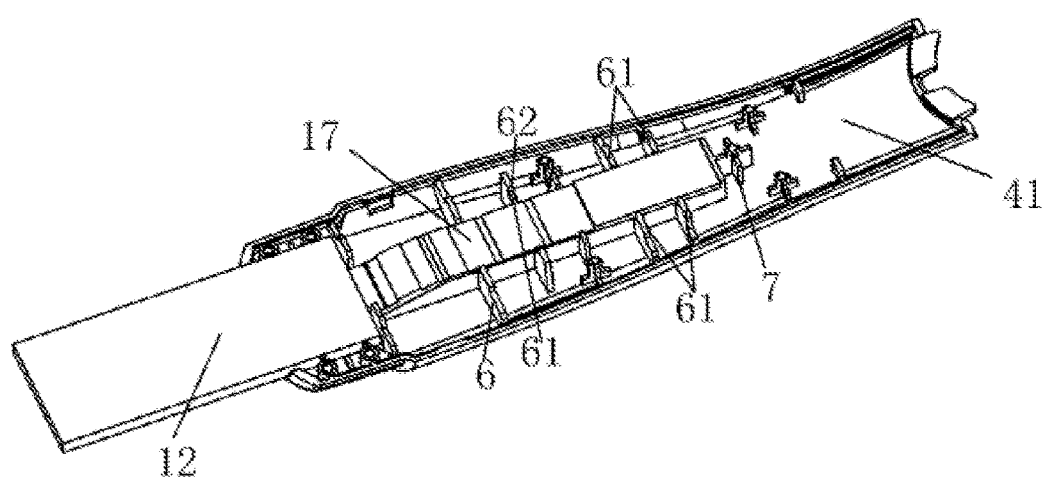
Figure 25:
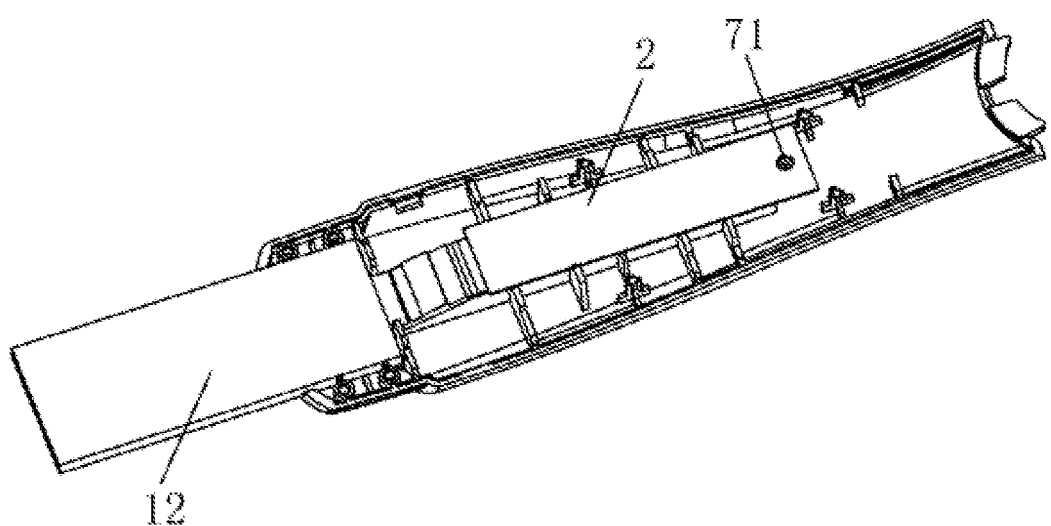

FIG. 1 is a schematic view of a detection device of the present invention;
FIG. 2 is a schematic view of another detection device of the present invention;
FIG. 3 is a schematic view of another detection device of the present invention;
FIG. 4 is a schematic view of another detection device of the present invention;
FIG. 5 is a schematic view of a specific detection device of the present invention;
FIG. 6 is a top view of the device of FIG. 5 (positive detection result display);
FIG. 7 is another top view of the device of FIG. 5 (negative detection result display);
FIG. 8 is an exploded schematic view of the device of FIG. 5;
FIG. 9 is a schematic view of another specific detection device of the present invention;
FIG. 10 is an exploded schematic view of the device of FIG. 9;
FIG. 11 is a schematic view of still another specific detection device of the present invention;
FIG. 12 is a front view of the detection device of FIG. 11;
FIG. 13 is a schematic view of another detection device of the present invention;
FIG. 14 is a cross-sectional view of the detection device of FIG. 13;
FIG. 15 is an exploded schematic view of the detection device of FIG. 13;
FIG. 16 is a schematic view showing the superimposed display of the result display area and the indicator area (positive detection result display);
FIG. 17 is a schematic view of another detection device of the present invention;
FIG. 18 is a schematic structural view of a detection cassette of the present invention;
FIG. 19 is an exploded schematic view of the detection cassette of FIG. 18;
FIG. 20 is another exploded schematic view of the detection cassette of FIG. 18;
FIG. 21 is a schematic view of another detection cassette of the present invention;
FIG. 22 is an exploded schematic view of the detection cassette of FIG. 21;
FIG. 23 is a partial enlarged view of FIG. 22A;
FIG. 24 is a schematic view showing the detection layer mounted on the bottom plate;
FIG. 25 is a schematic view showing the symbol display layer mounted on the bottom plate.

REFERENCE NUMBER

Detection device 10, sample detection layer 1, symbol display layer 2, indicator/indicator display symbol 21, liquid barrier layer/isolation pad 5, indicator region 23, (detection) result display region 18, detecting pad 17, gas generating pad 16, labelled pad 13, sample pad 12, water absorbing pad 8, bottom card 11, detection line 171, quality control line 172, adhesive block 3, detection cassette 40, bottom plate 41, cover plate 42, window 43, sample adding hole 45, space/gas channel 22, platform 6, support surface 61, blocking surface 62, positioning member 7, base 5, positioning hole 20, cover 46

DETAILED DESCRIPTION OF THE EMBODIMENTS

The structure involved in the present invention or these technical terms used therein will be further described below.
Detection
"Detection" means testing or measuring the presence of a substance or material, such as, but not limited to, a chemical substance, an organic compound, an inorganic compound, a metabolite, a drug or a drug metabolite, an organic tissue or a metabolite of an organic tissue, nucleic acid, protein or polymer. In addition, detection indicates the amount of test substance or material. Further, the test also indicates immunoassay, chemical detection, enzyme detection, etc.

Type of Sample

Any type of sample can be tested using the device of the present invention, including body fluids (e.g., urine and other body fluids, as well as clinical samples). Liquid samples may be derived from solid or semi-solid samples, including feces, biological tissues, and food samples. These solid and semi-solid samples can be converted into liquid samples by any suitable method, such as mixing, mashing, macerating, incubating, dissolving or enzymatically dissolving solid samples (e.g., water, phosphate buffer or other buffer) in a suitable liquid. "Biological samples" include samples derived from living animals, plants and food, as well as urine, saliva, blood and blood components, cerebrospinal fluid, vaginal swabs, semen, feces, sweat, secretions, tissues, organs, tumors, cultures of tissues and organs, cell cultures and conditional media there, whether human or animal. Food samples include processed food ingredients and final products, meat, cheese, wine, milk and drinking water. Plant samples include samples derived from any plant, plant tissue, plant cell culture, and conditional media there. "Environmental samples" are those samples derived from the environment (e.g., samples of lake water or other water, sewage samples, soil samples, groundwater samples, seawater samples, waste water samples). Sewage and related waste can also be included in environmental samples.

Type of Analyte

Examples of analytes that can be used in the stable detection of the present invention include, but are not limited to, human chorionic gonadotropin (hCG), luteinizing hormone (LH), ovarian estrogen (FSH), hepatitis C virus (HCV), hepatitis B virus (HBV), hepatitis B surface antigen, HIV and any drugs of abuse. The analyte can be detected in any liquid or liquefied sample, such as urine, saliva, blood, plasma or serum. Examples of other analytes are creatinine, bilirubin, nitrite, protein (non-specific), blood, white blood cells, blood sugar, heavy metals and toxins, bacterial components (e.g., special protein and sugar of specific types of bacteria, such as *E. coli* 0157:H7, *Staphylococcus aureus, Salmonella, Clostridium perfringens, Campylobacter, Listeria monocytogenes, Vaccina virus*, or *Bacillus cereus*). Any other analyte suitable for the lateral flow test mode can be detected by the device. The present invention will be further described in detail below with reference to the accompanying drawings and embodiments, but the scope of the invention is not limited thereto.

The detection device 10 of the present invention comprises two parts: a sample detection layer 1 and a symbol display layer 2; the symbol display layer 2 is treated with an indicator 21 which is capable of changing color; and the detection device 10 is formed by the combination of the two parts, as shown in FIG. 1. The detection device 10 can form an easily recognizable detection result or display of detection information after the sample is detected. Specifically, the symbol display layer 2 changes color by the indicator 21 to form a display symbol, the said display symbol may indicate detection information or detection result of the detection device 10. The shape of the indicator 21 treated on the symbol display layer 2 can be set as needed, so that the symbol displayed after changing the color is the same as the shape of the indicator, such as: number 1, 0, etc.; simple graphic, −, |, x, Δ, etc.; characters; letters Y, N, etc.; the symbol shape can be set using the indicator representation according to the needs of the detection device 10.

In some preferred embodiments, the indicator on symbol display layer 2 does not contact with sample detection layer 1. More specifically, the region 23 having the indicator on the symbol display layer 2 does not contact with the sample detection layer 1. As shown in FIGS. 2 and 3, the bottom surface of the symbol display layer 2 directly contacts the sample detection layer 1 and covers the sample detection layer 1, and at this time, the indicator 21 is treated on the upper surface of the symbol display layer 2 (i.e., the side not contacts with the sample detection layer). In a specific embodiment, a gas channel is provided between the sample detection layer and the symbol display layer; or, in another specific embodiment, a gas channel is provided between the result display area on the sample detection layer and the indicator area on the symbol display layer, as shown in FIG. 5, FIG. 9 and FIG. 11, and when the indicator 21 is treated on the side adjacent to the detection layer 1, then a gap or space 22 is provided between the symbol display layer 2 of the detection device 10 and the sample detection layer 1, making the indicator region 23 and the detection layer 1 not contact. The gap or space 22 is a gas channel 22 in which the gas volatilizes.

The position of the sample detection layer 1 and the symbol display layer 2 on the detection device 10 may be the position that the symbol display layer 2 covers on part or all of the sample detection layer 1. As shown in FIG. 2, the symbol display layer 2 covers on part of the sample detection layer 1; as shown in FIG. 3, the symbol display layer 2 covers on all of the sample detection layers 1. Alternatively, the sample detection layer 1 and the symbol display layer 2 are in the different positions of the detection device 10, i.e., they do not cover each other on the vertical projection surface.

After the indicator contacts with the gas and changes its color, the first color changes to a second color, and the symbol displayed by the second color can be used to indicate which detection item the detection device 10 is using. For example, in the detection device for drug abuse detection, the shape of the indicator of the symbol display layer is different, and in the detection device for detecting the morphine smoking condition, the shape of the symbol display layer on it is MOP (the abbreviation of morphine MOP). In the detection device for detecting the cocaine smoking condition, the shape of the symbol display layer indicator is COC (the abbreviation of cocaine COC). For example, in one embodiment, after the sample is added to the detection layer, because of the gas in the liquid sample itself or generated by the trigger of the sample, the indicator displays the symbol COC, indicating that the detected item of the detection device is cocaine.

The symbol displayed by the second color after the indicator changes color can also cooperate with the detection line of the sample detection layer to form an identifiable symbol that is easily understood by the users. In some specific embodiments, as shown in FIGS. 2 and 3, the sample detection layer 1 includes a result display area 18, and the indicator area 23 of the symbol display layer 2 corresponds to the position of the result display area 18 on the sample detection layer. That is, the position of the indicator area 23 and the position of the result display area 18 are spatially superimposed or overlapped. Thus, the color symbol formed by the indicator 21 can be superimposed on the detection line 171 on the sample detection layer 1, that is, the indicator color symbol and the detection line are vertically projected on a plane to form a new symbol, as shown in FIGS. 6 and 7 and FIG. 16, form one or more result display that are easy to understand and recognize. In FIG. 6, after the sample is added and when the analyte is present in the sample or the content of the analyte reaches a predetermined test value, a detection line 171 appears on the sample detection layer, and forms a "+" type symbol with the indicator 21 with color; in FIG. 7, after the sample is added and when the analyte is not present in the sample or the content of the analyte does not reach the predetermined test value, a detection line 171 does not appear on the result display area of the sample detection layer, and a "−" type symbol appears on the indicator 21 with color existed alone. Such symbols indicate that a result interpretation habit of people in positive and negative tests, and people are accustomed to using "+" for positive and "−" for negative. In the detection of the ordinary lateral side flow test strip, the detection result shows that a detection line is usually displayed or the detection line is not displayed, and in the judgment of the ordinary operator, the result is wrong due to unfamiliarity. In the present invention, a "+" or "−" symbol can be formed by superposition of the color symbol of the display reagent and the detection line. Of course, the superimposed detection results show that the symbol can also be varied. For example, the indicator displays "○", and forms "Φ", "Θ" or "○" with the detection result to display the opposite detection results such as positive and negative.

The indicator 21 of the symbol display layer displays the symbol by changing the color, which may change from one color to another, so that the operator acquires the detection information by the change of the color. For example, it changes from colorless to red, from light to dark, from red to green, blue, etc.; or, from red to colorless, from dark to light, etc. Specifically, in general, in the detection device in which the detection line exhibits a color that can be recognized, i.e. a positive result after the detection, the indicator usually changes from colorless to an easily observable color, or the first color of the indicator is the same as or similar to the background color of the detecting pad 17, and changes to the second color after detection in order not to make the operation mistaken the information. The indicator 21 adopts a color that is colorless or close to the background color of the pad and is not easily recognized by the users before the start of the detection, and compared with the color of the first color of the indicator which is easily recognized, this can prevent people misunderstanding that the detection device that is actually not used has been used. In the detection device in which the detection line exhibits a color that can be recognized i.e. a negative result, the indicator can change from an easily observable color to colorless, or the second color of the indicator is the same as or similar to the background color of the detecting pad.

The change of color is achieved by the indicator contacting with the gas to react. There are many types of such reactions that change color, for example, acid-base indication reaction.

The indicator is selected from acid-base indicators, such as nitrophenol, phenolphthalein, sulfonated phenol, azo compounds, etc.; specifically, such as p-nitrophenol, phenolphthalein, thymolphthalein, α-naphthol phenol red, cresol red, bromophenol blue, thymol blue, methyl orange, neutral red, etc. More specifically, for example, the indicator is selected from methyl orange, methyl red, etc. which is orange in an acidic environment and yellow in an alkaline environment; bromothymol blue, etc. which is yellow in an acidic environment and blue in an alkaline environment; phenolphthalein, etc. which is colorless in an acidic environment and red in an alkaline environment; litmus, etc. which is red in an acidic environment and blue in an alkaline environment. Different acid-base indicators can change color when encountering acid gases or alkaline gases in the corresponding reaction.

The gas that triggers the discoloration of the indicator 21 is generated by the gas generating reagent. Specifically, the gas may be generated by mixing different substances, or may be generated by mixing different substances with the liquid sample. These different substances do not mix with each other in the detection device 10 when not in use, they, at least not all of the substances are mixed together to prevent the gas from being generated and released in advance, so that the gas cannot contact with the indicator 21 on the detection device. For example, in the protocol where ammonia contacts with a bromophenol blue indicator to change the indicator from light yellow to blue, the ammonia generating substance includes ammonium chloride and an alkaline buffer salt. Ammonium chloride and an alkaline buffer salt are added at different positions of the detecting pad and does not contact with each other; or ammonium chloride and an alkaline buffer salt are separately added to different pads in the sample pad 12, the labelled pad 13 and the detecting pad 17; Alternatively, if the detection device 10 includes a gas generating pad, one of the ammonium chloride or alkaline buffer salts is added to the gas generating pad 16, and the other reagent is added to other locations through which the liquid flows, such as one or more of the sample pad 12, the labelled pad 13 or the detecting pad 17. Alternatively, when one of the ammonium chloride and the alkaline buffer salt is formulated into a solution, the other reactive reagent is added onto one or more of the sample pad 12, the labelled pad 13, the gas generating pad 16, or the detecting pad 17, and a solution reagent is added during detection to mix the ammonium chloride and the alkaline buffer salt to produce a gas. Alternatively, ammonium chloride and an alkaline buffer salt are formulated into a solution, and two solutions are added to the detection device during detection to be mixed to produce ammonia gas.

The gas produced can also be combined with moisture in the detection space to cause a color change in the indicator reaction.

In some embodiments, the acid indicator 21 on the symbol display layer 2 is discolored by the decomposition of an ammonium salt in an alkaline environment to produce ammonia gas. More specifically, for some samples having an ammonium salt itself such as urine sample, the ammonium salt in the sample is mixed with an alkaline buffer salt to produce ammonia gas while the sample is added to the detection device for detection, so that color of the acid indicator changes from the first color to the second color, and the indicator symbol is displayed, or the indicator is superimposed with the detection result line to form a result display symbol. In other embodiments, the ammonium salt may be treated in advance on the detection layer 1, and an alkaline buffer salt is added while the sample is added, so that the ammonium salt decomposes in an alkaline environment to release ammonia gas which makes the color of the indicator 21 change. In some preferred embodiments, the sample itself carries an ammonium salt. When the sample is added to the detection layer 1, the sample is localized in an alkaline environment to produce ammonia gas, and the color of indicator 21 changes from the first color to the second color. In some embodiments, the alkaline buffer salt is selected from borax, $NaCO_3$, $K_3PO_4$, etc.

In a more specific embodiment, as shown in FIG. 4, for the detection device 10, a liquid barrier layer 5 can be added between the sample detection layer 1 and the symbol display layer 2, and the function of the liquid barrier layer 5 is gas-permeable and water-impermeable. Also, the liquid barrier layer 5 is transparent. When the liquid sample is applied to the detection layer, the substance to be detected in the sample reacts with the substance pretreated on the detection layer 1 to form an obvious line, i.e. detection line. At the same time when the sample flows through the detection layer 1, the gas is released through the liquid barrier layer 5, making the indicator 21 treated on the symbol display layer 2 to be discolored to form a second color line. The line generated by the reaction of the substance to be tested forms a "+" or "−" with the indication line.

The material of the symbol display layer 2 can usually be a transparent or translucent material to facilitate observation of the covered detection result area. The symbol display layer 2 material can be selected as a water-impermeable material, and the symbol display layer 2 material can be selected as a gas-permeable or gas-impermeable material; the symbol display layer 2 can also be selected from a water-impermeable and gas-impermeable material; for example, a PTFE film, a gas-permeable and water-impermeable film, PET, PE, PP, etc. When the symbol display layer 2 is a gas-impermeable material, the indicator 21 is located on the side of the symbol display layer 2 adjacent to the sample detection layer. When the symbol display layer 2 is a gas-permeable material, the indicator 21 may be located on one side of the symbol display layer 2 adjacent to the sample detection layer or away from the sample detection layer, that is, the indicator 21 may be located on the front side or the back side of the symbol display layer. Of course, when the liquid barrier layer 5 is provided between the symbol display layer 2 and the sample detection layer 1, the material of the symbol display layer 2 may be selected from a water-permeable material.

In some embodiments, the sample detection layer 1 includes a detecting pad 17 having a detection result display area 18 thereon, and the symbol display layer 2 covers on the detecting pad 17, so that the indicator area 23 corresponds to the detection result display area 18, that is, the indicator area and the detection result display area are spatially overlapping or superimposed, as shown in FIG. 5. In this way, the indicator 21 can be superimposed with the detection result 171 to form an identifiable symbol, as shown in FIGS. 6 and 7.

As also shown in FIG. 5, in some embodiments, the sample detection layer 1 further includes a gas generating pad 16 for gas generation. For example, the gas generating pad 16 is treated with an ammonium salt. When the sample flows through the gas generating pad 16, the ammonium salt decomposes to form ammonia gas in an alkaline environment to change the color of the indicator 21.

In a more specific embodiment, the sample detection layer 1 further includes a labelled pad 13, a sample pad 12, and the sample pad 12 and the labelled pad 13 are sequentially connected upstream of the gas generating pad 16, and the gas generating pad 16 is connected upstream of the detecting pad 17. That is, the sample sequentially flows through the sample pad 12, the labelled pad 13, the gas generating pad 16, and the detecting pad 17. In another embodiment, the detection layer 1 further includes a water absorbing pad 8 connected downstream of the detecting pad 17 and a bottom card 11 to immobilize sample pad 12, a labelled pad 13, a gas generating pad 16 and a detecting pad 17, and the water absorbing pad 8. At this time, for example, the alkaline buffer salt can be treated on the sample pad 12, and after the sample is added to the sample pad 12, the alkaline buffer salt is caused to flow to reach the gas generating pad 16, so that the ammonium salt on the gas generating pad 16 decomposes to form ammonia in the in the alkaline environment.

In other embodiments, as long as the gas generated by the triggering of the gas generating pad 16 can contact the indicator 21 on the symbol display layer 2, the storage position of the gas generating pad 16 on the detection device 10 can be arbitrarily selected.

In some embodiments, one end of the symbol display layer 2 is connected with the sample pad 12 and the other end with the water absorbing pad 8 to form a space between the symbol display layer 2 and the labelled pad 13, the gas generating pad 16 and the detecting pad 17. This space is a gas channel, which is more beneficial to the diffusion of gas. This space can be either opened or closed.

In some embodiments, the symbol display layer 2 and the sample detection layer 1 may be fixedly connected, or may be a movable connection or a detachable connection. For example, the symbol display layer 2 is directly bonded and fixed to the sample detection layer 1; or the sample detection layer 1 is fixed on a bottom plate, and the symbol display layer 2 is fixed on a cover, and the symbol display layer 2 covers on the sample detection layer 1 when the cover and the bottom plate are closed, as shown in FIG. 20. Still alternatively, the end of the symbol display layer 2 is fixed to the sample detection layer 1 by a tearable adhesive strip, as shown in FIG. 11. In some more preferred embodiments, the symbol display layer 2 forms a certain space 22 with the sample detection layer 1 so that a certain distance is provided between the indicator region 23 of the symbol display layer and the detection layer 1, as shown in FIG. 5.

In some specific embodiments, the end protrusion 3 of the sample detection layer of the detection device is shown in FIG. 11, and the end of the symbol display layer is connected with protrusion 3, so that the symbol display layer 2 and the sample detection layer 1 are connected with each other and a space 22 is formed therebetween. Wherein, the indicator area superposes with the position of the result display area, as shown in FIGS. 11 and 16. The detection device of the present invention will now be described with respect to specific embodiments.

Embodiment 1: Detection Device Described in FIG. 5, FIG. 6, FIG. 7 and FIG. 8

A detection device 10 of lateral flow as shown in FIG. 5 for detecting hCG in urine, comprises a detection layer 1 and a symbol display layer 2, and the symbol display layer 2 covers over the detection layer 1, and a certain space is provided between the both as a channel 22 for gas volatilization. Specifically, the detection layer 1 comprises a bottom card 11 on which the sample pad 12, the labelled pad 13, the gas generating pad 16, the detecting pad 17 and the water absorbing pad 8 are sequentially adhered to each other, as shown in FIG. 5. One end of the symbol display layer 2 is bonded on the sample pad 12 and the other end on the water absorbing pad 8 to form a space 22 between the symbol display layer 2 and the labelled pad, the gas generating pad and the detecting pad. The sample pad 12 is used for receiving a test sample and the sample is transferred to a functional pad (e.g., a labelled pad, a detecting pad, etc.) downstream thereof. In the present embodiment, the labelled pad 13 is coated with a colloidal gold-labeled anti-hCG antibody (labeled antibody) which binds to the hCG antigen in the sample to form a first conjugate. In other embodiments, the different reagents are labeled on the labelled pad correspondingly, depending on the analyte. The detecting pad 17 is provided with at least a detection line 171. In the present embodiment, the detection line 171 is coated with hCG antibody, and the first conjugate flowing onto the detecting pad combines with the anti-hCG antibody on the detection line to form a line visible to the naked eye. If the hCG content in the urine is lower than the detected lowest threshold, no visible lines will be formed on the detection line. A quality control line 172 may also be included on the detecting pad 17, and the quality control line 172 is used to indicate whether the detection is successful or not.

Using different kinds of indicators shown in Table 1, a solution is prepared at a certain concentration. The prepared indicator solution is then separately treated on different transparent plastic sheets to form indication line 21 (the transparent plastic sheet in this example is the symbol display layer 2 of the present invention). For example: the indicator solution is sprayed on different transparent plastic sheets. The side of the transparent sheet having the indicator is made adjacent to the sample detection layer and assembled with the sample detection layer, and the indication line is located directly above the detecting line to form a cross.

In a specific embodiment, the width of the sample detection layer is 7.2 mm, and the width of the corresponding transparent sheet (symbol display layer) covering the sample detection layer is 7.2 mm, the width of the indicator is 1 mm, and the length is 8 mm.

In the present embodiment, an ammonium salt such as ammonium chloride or ammonium carbonate is formulated into an aqueous solution having a mass-to-volume ratio of 1%, and is treated on the gas generating pad 16 by immersion or the like, and the sample pad 12 is treated with an alkaline buffer salt. For example, the alkaline buffer salt is 100 mM Tris buffer, pH 8.0, and the sample pad is immersed in the buffer to obtain a sample pad with an alkaline buffer. The immersed gas generating pad and sample pad are assembled into the detection device in a dry state. When detected, the pH of the mixed solution is increased after the sample is mixed with the alkaline buffer salt of sample pad. When the ammonium salt in the gas generating pad contacts with the alkaline sample, the ammonium salt decomposes to form and release ammonia gas. The sample brings ammonia gas during the chromatography process, which contacts with the indicator of the transparent plastic sheet, and the indicator changes color.

When the hCG content in the sample is higher than the lowest detection value, a color line visible to the naked eye is formed on the detection line 171 of the detecting pad. The color line forms spatially a "+" symbol with the indication line on the symbol display layer 2. The detector can judge the sample as positive according to the "+" that appears, as shown in FIG. 6. If the hCG content in the urine is lower than the lowest detection value, a color line will not be formed on the detection line of the detecting pad, and only the indication line visible to the naked eye can appear on the detection line of the symbol display layer, so that a "–" symbol is formed, as shown in FIG. 7. The detector judges that the sample is negative according to "–".

Detection is performed using a urine standard containing 100 mIU/ml hCG. The color of the indication line 21 and the color of the detection line are recorded. The results are shown in Table 1.

TABLE 1

| Indicator | Solution ingredients | Initial color of indicator indication line | Reaction color of indicator indication line | Color level of indicator indication line |
|---|---|---|---|---|
| TCTB | ethanol solution containing 0.1% (mass-volume ratio) TCTB | light yellow | green | light color |
| bromo-cresol green | ethanol solution containing 0.1% (mass-volume ratio) bromo-cresol green | light yellow | green | developed significantly |
| brom-cresol purple | ethanol solution containing 0.1% (mass-volume ratio) brom-cresol purple | light yellow | dark purple | developed significantly |
| bromo-phenol blue | ethanol solution containing 0.1% (mass-volume ratio) bromo-phenol blue | light yellow | blue | developed significantly |

Each indicator can produce a significant color change after reaction. It also shows that the color strength is relatively suitable. Of course, in this embodiment, the ammonium salt can also be treated on the sample pad and the alkaline buffer salt is treated on the gas generating pad. When the urine sample is added to the sample pad, the ammonium salt flows with the sample to the gas generating pad to react with the alkaline buffer salt to generate ammonia gas.

Embodiment 2: Detection Device Described in FIG. 5, FIG. 6, FIG. 7 and FIG. 8

The structure of the detection device 10 in this embodiment 2 is identical to that of the embodiment 1, except that the alkaline buffer salt is not treated on the sample pad 12. In the process of the detection, after the sample is added, the liquid alkaline buffer salt sample pad 12 is immediately added. The alkaline buffer salt sequentially flows through the sample pad 12, the labelled pad 13, and reaches the sample generating pad 16 to decompose the ammonium salt into ammonia gas. The released ammonia gas combines with the indicator on the indication line 21 of the symbol display layer 2, causing the indicator 21 change color, forming a distinct indication line "–"; at the same time, the sample continues to flow through the gas generating pad 16 and reaches the detecting pad for detection. Thus, the detection result is obtained, that is, a detection line "|" is present or absent, thereby a symbol of "+" or "–" is displayed. In the hemoglobin test using human stool as a sample, the stool sample is diluted with an alkaline buffer to obtain a sample diluent, and the sample diluent is added to the sample pad of the detection device described in the present example. The alkaline buffer salt sequentially flows through the sample pad 12, the labelled pad 13, and reaches the sample generating pad 16 to decompose the ammonium salt into ammonia gas. The released ammonia gas combines with the indicator on the indication line 21 of the symbol display layer 2, causing the indicator 21 change color, forming a distinct indication line "–". The labelled pad 13 contains a latex-labeled anti-human hemoglobin antibody, and an antibody that specifically binds human hemoglobin is immobilized on the detecting pad. The diluent flows through the labelled pad, the gas generating pad 16, and reaches the detecting pad for detection, thereby obtaining a detection result, that is, a detecting line "|" is present or absent, thereby a symbol of "+" or "−" is displayed.

Of course, in this embodiment, after the sample is added to the sample pad 12, an alkaline buffer salt is added to the gas generating pad 16, and the alkaline buffer salt reacts with the ammonium salt on the gas generating pad 16 to generate ammonia. The ammonia gas contacts with the indicator 21 to change the color of the indicator 21.

Moreover, in the present embodiment, the ammonium salt may also be treated on the sample pad 12, and then the alkaline buffer salt is added to the sample pad 12 after the sample is added to the sample pad 12, so that the ammonium salt is reacted with the alkaline buffer salt to produce ammonia gas.

Alternatively, in the present embodiment, the ammonium salt may also be treated on the sample pad 12, and when the ammonium salt flows to the gas generating pad 16 with the sample after the sample is added to the sample pad, the alkaline buffer salt is added to the gas generating pad 16, so that the ammonium salt is reacted with an alkaline buffer salt to produce ammonia gas.

Embodiment 3: Detection Device Described in FIG. 9 and FIG. 10

The detection device 10 for detecting a urine sample as shown in FIG. 6 comprises a detection layer 1 and a symbol display layer 2, and the symbol display layer 2 covers on the detection layer 1. The said detection layer 1 comprises a bottom card 11, and the sample pad 12, the labelled pad 13, the detecting pad 17, and the water absorbing pad 8 are attached to each other on the bottom card 11 in sequence. One end of the symbol display layer 2 is bonded on the sample pad 12 and the other end on the water absorbing pad 8 to form a space 22 between the symbol display layer 2 and the labelled pad and the detecting pad. The detecting pad 17 comprises a detection line 171. The symbol display layer 2 is provided with an indication line 21 on the detection line 171 area on the detecting pad 17, and the mutual position relationship between the indication line 21 and the detection line 171 is crisscrossed. An indicator changing color when encountering ammonia gas, such as bromophenol blue, bromocresol green is contained at the position of the indication line.

In this embodiment, compared with the detection device in embodiment 1, a gas generating pad is not provided, and generally the self-contained ammonium salt in the liquid sample, or the ammonium salt added to the sample or added to the detection device during the detection is used to detect.

In the present embodiment, the sample pad 12 contains an alkaline buffer salt. When detected, the urine sample itself contains ammonium salts. As the urine passes through the sample pad 12, the pH of the urine sample increases under the action of the alkaline buffer salt of the sample pad 12. The ammonium salt in the urine decomposes in an alkaline environment to form ammonia gas and ammonia gas is released from the urine. The released ammonia gas diffuses to the symbol display layer 2, and combines with the indicator on the symbol display layer indication line 21, causing the indicator 21 change color, forming a distinct indication line "−", and combining the detection result to present "+" or "−", as shown in FIGS. 6 and 7.

Embodiment 4: Detection Device Described in FIG. 9 and FIG. 10

The detection device of embodiment 4 is identical to the detection device of embodiment 3 in structure, except that the sample pad 12 does not contain an alkaline buffer. When detected, after the urine sample is added to the sample pad 12, the alkaline buffer is added to the sample pad 12, and the ammonium salt in the urine decomposes with the action of the alkaline buffer salt to generate ammonia gas, and the ammonia gas released is combined with the indicator on the symbol display layer indication line, causing the indicator change color, forming a distinct indication line "−", and then combining the detection results to present a "+" or "−" symbol.

Embodiment 5

The device structure of embodiment 5 is the same as that of embodiment 1 or embodiment 3, except that the ammonium salt for generating gas may be separately added to the liquid passage before the detection line, such as the sample pad, the labelled pad, the gas generating pad or the detecting pad.

Embodiment 6

The device structure of the embodiment 6 is the same as that of the embodiment 1 or the embodiment 3. The ammonium salt and the alkaline buffer salt can be separately treated on the sample pad with a certain distance therebetween. That is, ammonium salt and the alkaline buffer salt do not contact before the sample is added to the sample pad, and after the sample flows on the sample pad, one of the ammonium salt and the alkaline buffer salt (the one flows upstream of the sample is treated) is carried to other place, and reacted between both and a gas is generated to change the color of the indicator.

Embodiment 7

The device structure of embodiment 7 is the same as that of embodiment 1, and the ammonium salt and the alkaline buffer salt can be separately treated on the gas generating pad with a certain distance therebetween. That is, the ammonium salt and the alkaline buffer salt do not contact before the sample flows onto the gas generating pad, and when the sample flows onto the gas generating pad, one of the ammonium salt and the alkaline buffer salt (the one flows upstream of the sample is treated) is carried to other place, and reacted between both and a gas is generated to change the color of the indicator.

Embodiment 8: Detection Device of Vertical Flow Described in FIGS. 11 and 12

In the design embodiment of FIGS. 11 to 12, the detection device 10 is a liquid vertical flow detection structure, comprising a symbol display layer 2 and a sample detection layer 1, the said symbol display layer 2 covers on the sample detection layer 1; wherein, the sample detection layer 1 comprises a bottom plate 11 and a detecting pad 17 which is on the bottom plate 11. The detecting pad 17 contains reagenta rereagent that reacts with the analyte; if necessary, the detecting pad 17 is also treated with a gas generating reagent such as an ammonium salt. The two end sides of the bottom plate have adhesive blocks 3. The symbol display layer 2 is adhered to the adhesive block and covers on the detecting pad 17. The adhesive block 3 may be such that one end of the symbol display layer is fixedly connected with the bottom plate 11 and the other end can be the movable connection that is torn and rebonded repeatedly, or two ends may also be movable connections which are torn and rebonded repeatedly. The symbol display layer 2 is treated with an acid-base indicator, and a space 22 is formed between the indicator 21 region and the detecting pad 17, and the symbol display layer 2 can be torn apart from the adhesive block. When tested, the end of the symbol display layer 2 movably connected with the adhesive block 2 is peeled off, the detecting pad 17 is exposed, and after the sample and/or the alkaline buffer salt is added to the detecting pad 17, then the symbol display layer 2 to be torn is again adhered to the adhesive block 3. When the substance to be analyzed is present in the sample, the detection line 171 appears on the detecting pad 17. At the same time, in an alkaline environment, the ammonium salt in the sample or treated on the detecting pad decomposes and releases the ammonia gas, and the generated ammonia gas contacts with the indicator on the symbol display layer, and the indication line 21 appears color, and a symbol of "+" or "−" is formed with the detection line 171. In FIG. 15, the indication line 21 forms "+" with the detection line 171.

In a more specific embodiment, the detection device 10 of vertical flow comprises a substrate pad, a gas generating pad, a reaction pad, an isolation pad 5, and an indicator pad 2. According to the characteristics of different products, the gas generating pad and the reaction pad can be combined into a layer as the detection layer 1. The function of the isolation pad 5 is gas permeable and water impermeable. After the liquid sample is loaded onto the detection device, the sample permeates through the substrate pad, the gas generating pad and the reaction pad. The substance to be tested present in the sample reacts with the substance pretreated on the reaction pad to form an obvious line. At the same time, when the sample flows through the substrate pad and the gas generating pad, ammonia gas is also released at the same time. Ammonia gas is transmitted through the isolation pad 5 to cause the indicator change color to form a distinct line. The line produced by the reaction of the substance to be tested forms a "+" with the indication line.

For example, in the detection product of saliva alcohol, the alcohol present in the sample reacts with the enzyme and substrate on the reaction pad to form a blue line. At the same time, when the sample flows through the substrate layer and the gas generating layer, ammonia gas is also released at the same time. The ammonia gas passes through the isolation pad to change the color of the indicator to form a distinct line. The lines produced by the alcohol reaction form a "+" with the indication lines.

Embodiment 9: Detection Device Described in FIG. 13, FIG. 14 and FIG. 15

In the design protocol shown in FIGS. 13 to 15, the detection device 10 is also a detection structure of vertical flow. Compared with the embodiment 8, the detection layer 1 includes a gas generating pad 16 in addition to the bottom plate 11 and the detecting pad 17, and the gas generating pad 16 and the detecting pad 17 are sequentially attached to the bottom plate 11. The gas generating pad 16 is treated with a gas generating substance such as an ammonium salt, etc. The adhesive blocks 3 are respectively located at both ends of the detecting pad 17, and the adhesive block 3 is covered with the symbol display layer 2 so that the symbol display layer 2 containing the indicator 21 covers on the detecting pad. The detecting pad 17 contains an reagent that reacts with the analyte. When testing, one end of the symbol display layer 2 connected with the adhesive block 3 is torn, and the detecting pad 17 is exposed. After the sample and/or the alkaline buffer salt is added to the detecting pad 17, the torn symbol display layer 2 is again adhered to the adhesive block 3. When the substance to be analyzed is present in the sample, the detection line 171 appears on the detecting pad 17. The sample continues to flow vertically downward, and after contacting with the gas generating pad, it contacts with the ammonium salt treated on the gas generating pad 16, and the ammonium salt decomposes to generate a gas, and the generated gas contacts with the indicator 21 on the symbol display layer, and the indication line appears, forming a "+" or "−" symbol with the detection line. In this embodiment, an ammonium salt and an alkaline buffer salt may be simultaneously treated on the gas generating pad 16, and the two are not treated together. When the sample flows onto the gas generating pad, the alkaline buffer salt mixes with the ammonium salt to generate a gas as the liquid flows.

Embodiment 10: Detection Device Described in FIG. 17

In the design shown in FIG. 17, the detection device 10 is opposite in position to the detection device 10 in FIG. 13, and the detection device includes, from top to bottom, the sample pad 12, the gas generating pad 16, the detecting pad 17, and the symbol display layer 2. The sample pad 12, the gas generating pad 16 and the detecting pad 17 constitute the detection layer 1. The sample is added onto the sample pad 12, and the sample sequentially flows into the gas generating pad 16 and the detecting pad 17. After the generated gas contacts with the symbol display layer 2, the indicator changes color, and superimposes with the detection line, indicating that the detection result is displayed as "+" or "−". Wherein, the ammonium salt can be treated on the sample pad 12, the gas generating pad 16 or the detecting pad 17, and similarly, the alkaline buffer salt can be treated on the sample pad 12, the gas generating pad 16 or the detecting pad 17. However, when the alkaline buffer salt and the ammonium salt are treated on the same pad, the two are not treated at the same position, so that the reaction does not occur in advance to generate a gas.

Embodiment 11: Detection Cassette of FIG. 18, FIG. 19 and FIG. 20

The detection cassette 40 shown in FIGS. 18 to 20 comprises a bottom plate 41, a cover plate 42, and a detection device 10, and the detection device 10 includes two parts, which are a sample detection layer 1 and a symbol display layer 2. The detection layer 1 may be a lateral flow test strip or a vertical flow test strip. The treatment substances and methods of the structure and components of the detection device 10 are also the same as those of the embodiments 1-10.

As shown in FIG. 19, the detection layer 1 is placed in the bottom plate 41 and fixed therein; the symbol display layer 2 is fixed in the cover plate 42; the cover plate 42 covers on the bottom plate 41, making the detection layer 1 and the symbol display layer 2 of the detection device 10 cover between the cover plate 42 and the bottom plate 41 of the detection cassette. The cover plate 42 has a sample adding hole 45, and the position of the sample adding hole 45 corresponds to the position of the sample pad 12, so that the position of the sample pad 12 is exposed at the sample adding hole 45 of the detection cassette 40, and the sample can be added to the sample pad 12 directly through the sample adding hole 45. The cover plate 42 also has a window 43 for observing the final detection results.

In other embodiments, the window 43 does not previously cover the transparent cover layer, but the symbol display layer 2 directly covers at the window 43, and the indicator 21 is applied at the symbol display layer 2 of the window position, and is located on the detection line 171.

The detection cassette 40 shown in FIG. 20 comprises an upper plate 41, a lower plate 42, and a detection layer 1. The window 43 covers on a transparent cover layer in advance, and the symbol display layer 2 is directly adhered to the window 43, and the indicator 21 is located at the window and above the detection line 171.

The detection cassette 40 shown in FIG. 19 includes an upper plate 41, a lower plate 42, and a detection device 10. The detection device 10 includes a sample detection layer 1 and a symbol display layer 2, and symbol display layer 2 is adhered to the sample detection layer 1 and has a certain gap with the sample detection layer 1. The detection device 10 is placed in the bottom plate 41, and the cover plate 42 covers on the bottom plate 41 so that the detection device 10 covers between the cover plate 42 and the bottom plate 41 of the detection cassette. The detection cassette 40 shown in FIGS. 18-20 includes an upper plate 41, a lower plate 42, and a detection device 10. Wherein, the detection device 10 is a vertical flow detecting test strip, more specifically selected from the detection devices shown in embodiments 6 to 8, and the vertical flow detecting test strips shown in FIGS. 11 and 12.

Embodiment 12: Screening Substrate Carrier for Gas Generation

Experiment Process:
a. The mass-to-volume ratio of 1% $NH_4Cl$ substrate solution is treated on Ahlstrom #8964 glass fiber, Whatman 3 MM filter paper, Ahlstrom #6613 polyester film and dried for future use.
b. The treated glass fiber, filter paper and polyester film are respectively used as sample pads of the test strip (such as the test strip in embodiment 1). A test strip to which no 1% $NH_4Cl$ substrate is added is used as a control.
c. 100 mIU/ml hCG urine standard is used to detect. The emerging time and color level of the indication line and the color of the detection line are recorded.
Experimental Results:

| | Experimental results | | | |
|---|---|---|---|---|
| Detection items | Without substrate (control) | Substrate treated on glass fiber | Substrate treated on filter paper | Substrate treated on polyester film |
| The emerging time of the indication line | 1'20" | 25-30" | 1' | 30-35" |
| The color level of the indication line | Light color | developed significantly | Light color | developed significantly |
| The color level of the detection line | Apparent detection line appears | Apparent detection line appears | Apparent detection line appears | Apparent detection line appears |

Conclusion: When the substrate is treated on different materials, it will affect the release rate of the substrate, thus affecting the emerging time and intensity of the indication line. In the comparative experiment, although no 1% $NH_4Cl$ substrate is added to the test strip. However, since the urine itself has an ammonium salt, when the urine contacts the alkaline buffer salt of the test strip, the ammonia gas is released and contacts with the indicator to change the color of the indicator. Also, since the concentration of the ammonium salt in the urine is low, the color of the indication line is lighter. When a gas generating pad with an ammonium salt substrate is added to the test strip, the disadvantages of the sample itself that the concentrations of the ammonium salt are not the same and the color of the indication line is not uniform are overcome. It ensures that the indication lines of different sample detection results are uniform and the color level is the same.

Embodiment 13: Effect of the Presence of the Indication Line on the Detection Line Experiment Process:
a. Experimental group: The transparent sheet of the indication line is treated and assembled with the detection layer with the gas generating pad to form a hCG test strip (cross signal hCG test strip).
Control group: Common hCG test strip (containing no substance which can change the color of the indicator on the symbol display layer) is simultaneously detected as a comparison.
b. Detection is performed with 25 mIU/ml and 100 mIU/ml hCG urine standards. The color level of the detection line is recorded.
Experimental Results:

| | Experimental results | |
|---|---|---|
| Detection reagent | 25 mIU/ml | 100 mIU/ml |
| Common hCG test strip | Faint detection line appears | Apparent detection line appears |
| Cross signal hCG test strip | Faint detection line appears | Apparent detection line appears |

Conclusion: The signal intensity of the detection line of the experimental group and the control group is consistent, which indicates that the presence of the indication line structure does not affect the detection line strength.

The sample type to which the said detection device described in the present invention can be applied includes a liquid sample such as urine, blood, saliva etc., or a sample which can be processed into a liquid and then detected, such as stool etc.

The discolored indicator of the present invention may also be a redox type indicator, and such an indicator may produce a color change when it encounters an oxidizing substance or a reducing substance of the corresponding reaction. For example, potassium dichromate itself is pale yellow, and it turns blue when it encounters ethanol gas.

Embodiment 14: Detection Cassettes of FIGS. 21, 22, 23, 24 and 25

The detection cassette 40 shown in FIGS. 21 to 25 comprises a bottom plate 41 and a cover plate 42 which can be assembled together, and a base 5 for placing the sample detection layer 1 is provided on the bottom plate 6, and platform 6 is provided on both sides of the base. The platform 6 includes a support surface 61 for carrying the symbol display layer 2, the support surface results in a gap or space 22 between the symbol display layer 2 and the sample detection layer 1 placed thereon, or at least the symbol display layer 2 does not contact with the detecting pad 17 on the detection layer 1.

In the embodiment shown in FIG. 22, a plurality of platforms are arranged on both sides of the base, so that both ends and the middle of the symbol display layer are supported to prevent a certain part of the symbol display layer from collapsing due to gravity to contact the sample detection layer. In the present embodiment, the platform 6 abuts against both sides of the base 5.

In a preferred embodiment, as shown in FIG. 23, the inner side wall of the platform 6 is further provided with a blocking surface 62 which is higher than the supporting surface 61. For example, the blocking surface 62 is vertically disposed on the supporting surface 61. When the symbol display layer 2 is placed on the support surface 61 of the platform 6, the blocking surface 62 is located outside the side of the symbol display layer 2, and the platform blocking surface 62 can prevent the symbol display layer 2 sliding out from both sides of the platform 6. In the embodiment shown in FIG. 22, a plurality of platforms 6 are provided on both sides of the base 5, and the platform 6 includes two types with a blocking surface and without a blocking surface. For example, five platforms 6 are symmetrically arranged on both sides of the base 5, and one of the platforms 6 includes a blocking surface.

In a more preferred protocol, the detection cassette 40 is provided with a positioning member 7 for positioning the position of the symbol display layer at the detection cassette to further ensure that the symbol display layer 2 is in the correct position, and make the indicator 21 on the symbol display layer 2 intersect with the detection line 171 on the detecting pad on the projection plane. In the example shown in FIG. 22, the positioning member 7 is a cross pin with a bump 71. The position of the symbol display layer 2 relative to the positioning member 7 is provided with a positioning hole 20.

In the embodiment shown in FIG. 22, the detection layer 1 is a lateral flow test strip comprising a sample pad 12, a labelled pad 13, a detecting pad 17, and a water absorbing pad 8, wherein the labelled pad, the detecting pad and the water absorbing pad are superposed on each other and adhered to the bottom card, and the sample pad 12 is bonded with the labelled pad 12. As shown in FIG. 24, the labelled pad, the detecting pad and the water absorbing pad of the detection layer 1 and the bottom card thereof are assembled in the base 5 of the bottom plate 41. platform 6 is provided on both sides of the base 5, and the positioning members 7 are mounted on the bottom plate 41 at the end of the water absorbing pad 8. The symbol display layer 2 is placed on the platform 6, and the support surface 61 supports the symbol display layer 2 and does not contact with the detection layer 1; the blocking surface 62 of the platform 6 is stuck on the outer side of the detection layer 1, thereby restricting the detection layer 1 on the platform 6; the bump 71 of the positioning member 7 is stuck in the positioning hole 20 of the symbol display layer, as shown in FIG. 25, which not only avoids the movement of the symbol display layer 2, but also assembles the symbol display layer 2 to the correct position relative to the detection layer 1. A window 43 is opened on the cover plate 42 at a position relative to the detection line and the quality control line. The bottom plate 41 and the cover plate 42 are engaged with each other, and the labelled pad 13, the detecting pad 17, the water absorbing pad 18 and the symbol display layer 2 are located in the engaged cavity. A part of the sample pad 17 is located outside of the cavity in which the bottom plate 41 and the cover plate 42 are engaged. The cover 46 is sleeved at the front end of the cavity, and the sample pad 12 is located inside the cover 46.

The indicator display layer 2 is treated with an indicator; after the indicator contacts with a gas which can change the color of the indicator, the indicator changes from the first color to the second color. The reagents that trigger the generation of the gas are added in the same manner as the previous embodiments.

When used, the removal of cover 46 exposes the sample pad 12 and the urine sample is applied directly to the exposed sample pad 12. When the HCG value in the urine sample is larger than a predetermined threshold value, the color development of the detection line and the indicator display symbol 21 on the symbol display layer form a detection result of a "+". When the HCG in the urine sample is less than a predetermined threshold, the detection line is not developed or is not easily observed by the naked eye, and only the indicator display symbol 21 on the symbol display layer develops, forming a detection result of the "−".

What is claimed is:

1. A detection device to determine the presence or absence of an analyte in a sample, comprising:
    a sample detection layer comprising a sample pad, a labelled pad, a gas generating pad and a detecting pad operably connected sequentially such that the sample, when applied to the sample pad, flows sequentially through the sample pad, the labelled pad, the gas generating pad, and the detecting pad,
        wherein the labelled pad comprises a first detecting reagent that reacts with the analyte to form a complex, wherein the detecting reagent comprises a visually detectable label,
        wherein the detecting pad comprises a second detecting reagent that reacts with the analyte, wherein a complex formed by the first detecting reagent, the analyte, and the second detecting reagent produces a color change on a result display region of the detecting pad to provide a first visually detectable symbol, and
        wherein the gas generating pad comprises a gas generating reagent that reacts with a material in the sample that is not the analyte to generate a gas; and
    a symbol display layer comprising an indicator configured to be contacted by the generated gas and thereby produce a color change on the symbol display layer to provide a second visually detectable symbol.

2. The detection device according to claim 1, wherein the indicator does not contact the result display region.

3. The detection device according to claim 2, wherein a gas channel is provided between the result display region and the symbol display layer.

4. The detection device according to claim 3, wherein the result display region and the symbol display layer are configured such that the first and second visually detectable symbols are spatially superimposed or overlapping overlap.

5. The detection device according to claim 4, wherein the symbol display layer is located above the sample detection layer, the symbol display layer is a formed of transparent or translucent material, and the first and second visually detectable symbols together form an identifiable symbol.

6. The detection device according to claim 5, wherein a liquid barrier layer is provided between the sample detection layer and the symbol display layer, and the liquid barrier layer is formed of a transparent gas-permeable, water-impermeable material.

7. The detection device according to claim 1, wherein the indicator is an acid-base indicator and the gas generating reagent is an acid-base reaction generating reagent.

8. The detection device according to claim 7, wherein the acid-base indicator is selected from bromothymol blue, bromocresol green, and phenolphthalein; and the acid-base reaction generating reagent is selected from an alkaline buffer salt or a combination of an ammonium salt and an alkaline buffer salt.

9. The detection device according to claim 8, wherein said acid-base reaction generating reagent is the combination of an ammonium salt and an alkaline buffer salt, and the detection device is configured such that the ammonium salt and the alkaline buffer salt do not contact each other before the sample is added to the sample detection layer.

10. The detection device according to claim 9, wherein the ammonium salt and the alkaline buffer salt are independently provided on the gas generating pad, wherein the ammonium salt and the alkaline buffer salt are spatially separated.

11. The detection device according to claim 1, wherein the sample detection layer further comprises a water absorbing pad operably connected downstream of the detecting pad.

\* \* \* \* \*